US010125348B2

(12) United States Patent
Beliaev et al.

(10) Patent No.: US 10,125,348 B2
(45) Date of Patent: Nov. 13, 2018

(54) MICROBIAL CONSORTIA FOR PROGRAMMABLE OUTPUT VIA PHOTOAUTOTROPH-HETEROTROPH INTERACTIONS

(71) Applicant: Battelle Memorial Institute, Richland, WA (US)

(72) Inventors: Alex S. Beliaev, Richland, WA (US); Ryan S. McClure, Richland, WA (US); Hans C. Bernstein, Richland, WA (US); Stephen R. Lindemann, West Richland, WA (US); G. Chris Jansson, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 3 days.

(21) Appl. No.: 14/991,263

(22) Filed: Jan. 8, 2016

(65) Prior Publication Data

US 2016/0201026 A1    Jul. 14, 2016

Related U.S. Application Data

(60) Provisional application No. 62/101,492, filed on Jan. 9, 2015, provisional application No. 62/101,496, filed on Jan. 9, 2015.

(51) Int. Cl.
| | | |
|---|---|---|
| *C12N 1/20* | (2006.01) | |
| *C12Q 1/68* | (2018.01) | |
| *C12Q 1/6874* | (2018.01) | |
| *C12N 1/00* | (2006.01) | |
| *C12N 1/38* | (2006.01) | |
| *C12N 15/115* | (2010.01) | |
| *C12N 15/63* | (2006.01) | |

(52) U.S. Cl.
CPC ............... *C12N 1/20* (2013.01); *C12N 1/00* (2013.01); *C12N 1/38* (2013.01); *C12N 15/115* (2013.01); *C12N 15/635* (2013.01); *C12Q 1/6874* (2013.01); *C12N 2310/16* (2013.01); *C12N 2320/13* (2013.01)

(58) Field of Classification Search
None
See application file for complete search history.

(56) References Cited

U.S. PATENT DOCUMENTS 8,518,690 B2    8/2013 Beliaev et al.

OTHER PUBLICATIONS

Beliaev et al., "Inference of Interactions in Cyanobacterial-Heterotrophic Co-cultures via Transcriptome Sequencing," *ISME J.* 8:2243-2255, 2014.
Brenner et al., "Engineering Microbial Consortia: A New Frontier in Synthetic Biology," *Trends Biotechnol.* 26:483-489, 2008.
Kong et al., "Programming the Group Behaviors of Bacterial Communities with Synthetic Cellular Communication," *Bioresources and Bioprocessing* 1:24, 2014 (11 pages).
Lindemann et al., "Engineering Microbial Consortia for Controllable Outputs," *ISME J.*, Advance Online Publication, pp. 1-8, Mar. 2016.
Lynch et al., "A High-Throughput Screen for Synthetic Riboswitches Reveals Mechanistic Insights Into Their Function," *Chem Biol.* 14:173-184, 2007.
PCT/US2016/012594 Invitation to Pay Additional Fees with Partial International Search Report, dated Jun. 6, 2016 (8 pages).
Balagaddeé et al., "A synthetic *Escherichia coli* predator-prey ecosystem," *Mol Syst Biol* 4:187, 2008 (8 pages).
Beliaev et al., "Interference of interactions in cyanobacterial-heterotrophic co-cultures via transcriptome sequencing," *ISME J* 8:2243-2255, 2014.
Brenner et al., "Engineered bidirectional communication mediates a consensus in a microbial biofilm consortium," *Proc Natl Acad Sci USA* 104(44):17300-17304, 2007.
You et al., "Programmed population control by cell-cell communication and regulated killing," *Nature* 428:868-871, 2004.
Bernstein et al., Synthetic *Escherichia coli* Consortia Engineered for Syntrophy Demonstrate Enhanced Biomass Productivity, *J. Biotechnol.* 157:159-166, 2012.
Brenner et al., "Engineering microbial consortia: a new frontier in synthetic biology," *Trends Biotechnol* 26(9):483-489, 2008.
Chiu et al., "Emergent Biosynthetic Capacity in Simple Microbial Communities," *PLOS Comput. Biol.* 10:e1003695, 2014.
Edwards et al., "Riboswitches: A Common RNA Regulatory Element," *Nature Education* 3(9):9, 2010.
Garst et al., "Riboswitches: Structures and Mechanisms," *Cold Spring Harb Perspect Biol.* 3:a003533, 2011.
Goers et al., "Co-Culture Systems and Technologies: Taking Synthetic Biology to the Next Level," *J. R. Soc. Interface* 11:2014065, 2014.
Jagmann and Philipp, "Design of synthetic microbial communities for biotechnological production processes," *J Biotechnol* 184:209-218, 2014.
Jin and Huang, "Engineering a Portable Riboswitch-LacP Hybrid Device for Two-Way Gene Regulation," *Nucl. Acids Res.* 39(19):e131, 2011.
Kazanov et al., "Abundance and Functional Diversity of Riboswitches in Microbial Communities," *BMC Genomics* 8:347-355, 2007.
Lynch et al., "A High Throughput Screen for Synthetic Riboswitches Reveals Mechanistic Insights into their Function," *Chem. Biol.* 14(2):173-184, 2007.
Lynch and Gallivan "A Flow Cytometry-Based Screen for Synthetic Riboswitches," *Nucl. Acids Res.* 37(1):184-192, 2009.
Lynch et al., "High-Throughput Screens to Discover Synthetic Riboswitches," *Riboswitches, Methods Mol Biol* 540:321-333, 2009.
Macia and Sole, "How to Make a Synthetic Multicellular Computer," *PLoS ONE* 9(2):e81248, 2014.

(Continued)

*Primary Examiner* — Nancy A Treptow
(74) *Attorney, Agent, or Firm* — Klarquist Sparkman, LLP

(57) ABSTRACT

Self-sustained, safe, stable and scalable microbial consortia ($S^5$MicroCon) are described. The microbial consortia are regulated by photoautotroph-heterotroph interactions and RNA aptamer-based gene circuits. A rapid, high-throughput method for engineering RNA aptamer-based gene circuits (e.g. riboswitches) is also described.

13 Claims, 9 Drawing Sheets

Specification includes a Sequence Listing.

(56) References Cited

OTHER PUBLICATIONS

Muranaka et al., "An Efficient Platform for Genetic Selection and Screening of Gene Switches in *Escherichia coli*," *Nucl. Acids Res.* 37(5):e39, 2009.
Tanouchi et al., "Engineering Microbial Systems to Explore Ecological and Evolutionary Dynamics," *Curr. Opin. Biotechnol.* 23(5):791-797, 2012.
Wittmann and Suess, "Engineered Riboswitches: Expanding Researchers' Toolbox with Synthetic RNA Regulators," *FEBS Lett.* 586:2076-2083, 2012.
Xia et al., "Succinate Production from Xylose-Glucose Mixtures using a Consortium of Engineered *Escherichia coli*," *Eng. Life Sci.* 15:65-72, 2015.

SEQUENCE LISTING

<160> NUMBER OF SEQ ID NOS: 32

<210> SEQ ID NO 1
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 1
tggggatgtg catgg                                                          15

<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 2
tcgatggggt atacg                                                          15

<210> SEQ ID NO 3
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 3
acgcctggcg gtcag                                                          15

<210> SEQ ID NO 4
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 4
tttggttgtt tgttg                                                          15

<210> SEQ ID NO 5
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 5
tggtgaagta ggcgg                                                          15

<210> SEQ ID NO 6
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 6
gtgccttcag tactg                                                          15

<210> SEQ ID NO 7
<211> LENGTH: 15
<212> TYPE: DNA
<213> ORGANISM: Artificial Sequence

```
<220> FEATURE:
<223> OTHER INFORMATION: Synthetic polynucleotide

<400> SEQUENCE: 7
cgtggtgggt agctg                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 8
gaactcgatt tcggg                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 9
caggataggg tcgcc                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 10
caggatgcgg tcgcc                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 11
caggatgggc tcgcc                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 12
caggatgggg gcacc                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 13
caggatgggg tcccc                                                    15
```

<210> SEQ ID NO 14
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 14
caggatgggg tggcc                                                        15

<210> SEQ ID NO 15
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 15
cagggtgggc tcgcc                                                        15

<210> SEQ ID NO 16
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 16
ccacgtgggc aggcc                                                        15

<210> SEQ ID NO 17
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(2)
<223> OTHER INFORMATION: n = a or c
<220> FEATURE:
<221> NAME/KEY: misc_feature
<222> LOCATION: (3)..(3)
<223> OTHER INFORMATION: n = g or a
<220> FEATURE:
<221> NAME/KEY: misc_feature
<222> LOCATION: (4)..(4)
<223> OTHER INFORMATION: n = g or c
<220> FEATURE:
<221> NAME/KEY: misc_feature
<222> LOCATION: (5)..(5)
<223> OTHER INFORMATION: n = a or g
<220> FEATURE:
<221> NAME/KEY: misc_feature
<222> LOCATION: (7)..(7)
<223> OTHER INFORMATION: n = g or a
<220> FEATURE:
<221> NAME/KEY: misc_feature
<222> LOCATION: (8)..(8)
<223> OTHER INFORMATION: n = g or c
<220> FEATURE:
<221> NAME/KEY: misc_feature
<222> LOCATION: (10)..(10)
<223> OTHER INFORMATION: n = g or c
<220> FEATURE:
<221> NAME/KEY: misc_feature
<222> LOCATION: (11)..(11)
<223> OTHER INFORMATION: n = t, g or a
<220> FEATURE:
<221> NAME/KEY: misc_feature
<222> LOCATION: (12)..(12)
<223> OTHER INFORMATION: n = c or g

```
<220> FEATURE:
<221> NAME/KEY: misc_feature
<222> LOCATION: (13)..(13)
<223> OTHER INFORMATION: n = g, c or a

<400> SEQUENCE: 17
cnnnntnngn nnncc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 18
ggttgtcctt aagat                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 19
ggttgtgcat aagat                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 20
ggttgtgcct aagat                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 21
ggttgtgcgc aagat                                                    15

<210> SEQ ID NO 22
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 22
ggttgtgctt aaggt                                                    15

<210> SEQ ID NO 23
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 23
```

```
ggttgtgctt atgat                                              15

<210> SEQ ID NO 24
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 24
ggttgtgctt gagat                                              15

<210> SEQ ID NO 25
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 25
ggttgtgttt aagat                                              15

<210> SEQ ID NO 26
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 26
ggttttgcgt aagat                                              15

<210> SEQ ID NO 27
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: n = g or t
<220> FEATURE:
<221> NAME/KEY: misc_feature
<222> LOCATION: (7)..(7)
<223> OTHER INFORMATION: n = g or c
<220> FEATURE:
<221> NAME/KEY: misc_feature
<222> LOCATION: (8)..(8)
<223> OTHER INFORMATION: n = c or t
<220> FEATURE:
<221> NAME/KEY: misc_feature
<222> LOCATION: (9)..(9)
<223> OTHER INFORMATION: n = t, g, c or a
<220> FEATURE:
<221> NAME/KEY: misc_feature
<222> LOCATION: (10)..(10)
<223> OTHER INFORMATION: n = t or c
<220> FEATURE:
<221> NAME/KEY: misc_feature
<222> LOCATION: (11)..(11)
<223> OTHER INFORMATION: n = a or g
<220> FEATURE:
<221> NAME/KEY: misc_feature
<222> LOCATION: (12)..(12)
<223> OTHER INFORMATION: n = a or t
<220> FEATURE:
<221> NAME/KEY: misc_feature
<222> LOCATION: (14)..(14)
<223> OTHER INFORMATION: n = a or g

<400> SEQUENCE: 27
```

```
ggttntnnnn nngnt                                                    15

<210> SEQ ID NO 28
<211> LENGTH: 104
<212> TYPE: DNA
<213> ORGANISM: Artificial Sequence
<220> FEATURE:
<223> OTHER INFORMATION: Synthetic polynucleotide

<400> SEQUENCE: 28
attgtgagcg gataacaatt actagagata cgactcacta taggtaccgg tgataccagc    60
atcgtcttga tgcccttggc agcaccctga aaggggcaa caag                    104

<210> SEQ ID NO 29
<211> LENGTH: 201
<212> TYPE: DNA
<213> ORGANISM: Artificial Sequence
<220> FEATURE:
<223> OTHER INFORMATION: Synthetic polynucleotide

<400> SEQUENCE: 29
acgacgacag gcacccgaac tctctagagg gcgaaagccg gcgcgtcctg gattccacca    60
agcatgtccc taccatacgg gattgcccag cttcggctgc catgccggcc aaacggtaac   120
cggcctacgg gagggtaca caacgctgat gagtcccaaa taggacgaaa cgcgctagat    180
ctgaaagagg agaaatacta g                                            201

<210> SEQ ID NO 30
<211> LENGTH: 2032
<212> TYPE: DNA
<213> ORGANISM: Artificial Sequence
<220> FEATURE:
<223> OTHER INFORMATION: Synthetic polynucleotide

<400> SEQUENCE: 30
atgcgtaccc tgctgattga taactatgat agctttaccc acaacctgtt tcagtatatc    60
ggtgaagcaa ccggtcagcc tccggttgtt gttccgaatg atgcagattg agccgtctg   120 ccgctggaag attttgatgc aattgttgtt agtccgggtc cgggtagtcc ggatcgtgaa   180
cgtgattttg gtattagccg tcgtgcaatt accgatagcg gtctgccggt tctgggtgtt   240
tgtctgggtc atcagggtat tgcacagctg tttggtggca ccgttggtct ggcaccggaa   300
ccgatgcatg gtcgtgttag cgaagttcgt cataccggtg aagatgtttt tcgtggtctg   360
ccgagcccgt ttaccgcagt tcgttatcat agcctggcag caaccgatct gccggatgaa   420
ctggaaccgc tggcctggtc agatgatggt gttgttatgg gtctgcgtca tcgtgaaaaa   480
ccgctgtggg caagcagcag caccggtgtt catcgtcagc gtctgcgtcc gggtgatcat   540
ggtcagctgc ctcgtccgcg tccacgtccg cctccgggta caagtcgtcg tggtcgtctg   600
cctgttcgta caccgcgtgc accgcgtcgt cgtgcagcag gtcgtcgtcg cggtactccg   660
cgtctgccag cacgtcctcg tgctccgcgt agcggttgga ccgcagcacc gagcagcaaa   720
gcaccgcgtg tactgctgcc acgtcgtcgc cctcgtccgg cacgtcgtgt tccgcatctg   780
cctcgccgtc gtcggcgtcg cctgcgtcct ggctgcgtc gtcatcatga tccgggtcgt   840
ggtgatccgc tgcagctgcc tggtggtgca gcacgtacag ccggtggtag tcgccgtcct   900
cgtcctgccc tgcgtgttca gccacgtctg cgtcgtctgc cacgcctgcg tgccgaaggt   960
ggtgatcatc gtcgtcctcg tagcaccggt ccggctccgg ctcgccgtgt tcctctgcgt  1020
```

| | |
|---|---|
| cgcccacgtc atcgtcctcg cccacctgga cgtctgctgc tgcctgcagg accgcgtcct | 1080 |
| cctggtccac gtcgccgtcg gccacggctg gcagctggtg atggtcgcga tccgcatcgt | 1140 |
| cctggccgtc cacgccctgc cgaagcagat ccgcgtcatg gtctgcgtgg tccgcgtggt | 1200 |
| ggtggacggc tgcgtcctcc aggtagccgt accccctcgtc agggtcgtct gggtgctccg | 1260 |
| cagcgtcgtg ttgtgcgtga tctgcctgat cagcatggtc atcgtgcaga tcgtggtgac | 1320 |
| ggtccggcag cactgctgcg tgcggcacct catcaaccgc gtccggtttg cgtcctgca | 1380 |
| cgcgttccgc gtgcagttgg tgcacagcgt ctggcacgtg cagttccgca tgatcggcgt | 1440 |
| cgtcgtcgcc gtcgtgttca ggcacatcag ggtgatccgc caccgggtcg taccggtggt | 1500 |
| ggcggtcgtg ccgcacctcg tcgtccaggt cgtcctggtg aaggtcctgg tcgtgaaccg | 1560 |
| gatgatcgcc gtccgggacc tcagcgtcct cagcagcggc tgcgtgatcg tctgcgtcct | 1620 |
| cgtgcccctg cactgcgtgg tggtcgtcca cgtgctcgtg caccggcagg cgttgatcat | 1680 |
| cctggcaccg cagcagcccg tcatcagcat cgtcggctgc gcacacgcg tctgcctcgt | 1740 |
| cgtctgcatg atcgtcgtgc acaagaggca acccatggtg accaccgtcc tccgggtggt | 1800 |
| cgccctccag gccgtctgac acgtggtgca cgtatggttc gtccgcaacg ccgtcgccgt | 1860 |
| ccgcagcatc gtcatccgca tcatcgtgcc ggtcgtcggc ctggtcgcgt tcggcgtcgg | 1920 |
| cgtggggatc gtgtaccact gcgtcctggc ggtggtgtgc aggccgatcg tggtcagggt | 1980 |
| cctcgtcatg gccatcgtcc acggcgtcag cgtagtggtg gccgtccgat ga | 2032 |

<210> SEQ ID NO 31
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 31

| | |
|---|---|
| atgaccgaac agaatgaact gcaggttgca gcagcacgtg gtgcacgtcg tccgcgtcgt | 60 |
| gatgcaagcg gtcatggtgc agcaccgcat cgtcctcgtt gtccgcatcg tgcagttcag | 120 |
| gttccggcac gccgtccgga tgatgcagca cgtcctggtc agccaggtca gggccagggt | 180 |
| cgtcctctgc gtcgtcgtcc acgtcctcgt cgtattgttc cgggtgaacc gctgcgtcgc | 240 |
| gatcatcatg gtgatgttcc gcgtcgcggt ccgggtgatg aacctggtga accggatggc | 300 |
| cgtggtcctg gcgaaccggt tatgtattaa | 330 |

<210> SEQ ID NO 32
<211> LENGTH: 987
<212> TYPE: DNA
<213> ORGANISM: Artificial Sequence
<220> FEATURE:
<223> OTHER INFORMATION: Synthetic polynucleotide

<400> SEQUENCE: 32

| | |
|---|---|
| atgagcggtt ttccgcgctag cgttgttgtt ggtggtagcg gtgcagtggg tggtatgttt | 60 |
| gcaggtctgc tgcgtgaagc aggtagccgt accctggttg ttgatctggt tccgcctccg | 120 |
| ggtcgtccgg atgcatgtct ggttggtgat gttaccgcac cgggtccgga actggcagca | 180 |
| gcactgcgtg atgcagatct ggtgctgctg gccgttcatg aagatgttgc actgaaagca | 240 |
| gttgcaccgg ttacccgtct gatgcgtccg ggtgcactgc tggcagatac cctgagcgtt | 300 |
| cgtaccggta tggcagcaga gctggcagca catgcaccgg tgttcagca tgttggtctg | 360 |
| aatccgatgt ttgcaccggc agcaggtatg acaggccgtc cggttgcagc agttgttacc | 420 |

```
cgtgatggtc ctggtgtgac cgcactgctg cgtctggttg aaggtggtgg tggtcgtcct    480
gttcgtctga cagccgaaga acatgatcgt accaccgcag caacccaggc actgacccat    540
gcagttattc tgagctttgg tctggcactg gcacgtctgg gtgttgatgt tcgtgcactg    600
gcagccaccg caccgcctcc gcatcaagtt ctgctggccc tgctggcacg tgttctgggt    660
ggtagtccgg aagtttatgg tgatattcag cgtagcaatc cgcgtgcagc aagcgcacgt    720
cgtgccctgg ctgaagccct gcgtagctttt gcagcactga ttggtgatga tcctgatcgt    780
gccgaagatc cggaccgtgc agatgacccg gatcgtaccg ataatcctgg tcatccgggt    840
ggttgtgatg gtgcaggtaa tctggatggt gtttttgaag aactgcgtcg cctgatgggt    900
cctgagctgg ctgcaggcca ggatcattgt caagaactgt ttcgtaccct gcatcgtaca    960
gatgatgaag gtgaaaaaga tcgctaa                                        987
```

MICROBIAL CONSORTIA FOR PROGRAMMABLE OUTPUT VIA PHOTOAUTOTROPH-HETEROTROPH INTERACTIONS

CROSS REFERENCE TO RELATED APPLICATIONS

This application claims the benefit of U.S. Provisional Application No. 62/101,496 and U.S. Provisional Application No. 62/101,492, both filed Jan. 9, 2015, which are herein incorporated by reference in their entirety.

ACKNOWLEDGMENT OF GOVERNMENT SUPPORT

This invention was made with government support under contract number DE-AC05-76RL01830 awarded by the U.S. Department of Energy. The government has certain rights in the invention.

FIELD

This disclosure concerns a rapid, high-throughput method for engineering RNA aptamer-based gene circuits. This disclosure further concerns self-sustaining microbial consortia regulated by photoautotroph-heterotroph interactions and RNA aptamer-based gene circuits.

BACKGROUND

Riboswitches are RNA-encoded genetic control elements that regulate gene expression in a ligand-dependent fashion. They are comprised of an aptamer domain, which recognizes the ligand, and an expression platform, which couples ligand binding to changes in gene expression. Natural riboswitches are found commonly in prokaryotes, and sometimes in eukaryotes (Lynch et al., *Chem Biol* 14(2):173-184, 2007). In addition, a number of synthetic riboswitches that respond to non-endogenous small molecules have been developed (Desai et al., *J Am Chem Soc* 126:13247-13254, 2004; Grate et al., *Bioorg Med Chem* 9:2565-2570, 2001; Harvey et al., *RNA* 8:452-463, 2002; Suess et al., *Nucl Acids Res* 31:1853-1858, 2003; Werstruck et al., *Science* 282:296-298, 1998). Synthetic riboswitches can be used, for example, to construct synthetic gene circuits, to report on cellular metabolism, or to reprogram cellular behavior (Lynch et al., *Methods Mol Biol* 540:321-333, 2009).

A microbial consortium is a group of different species of microorganisms that act together as a community. Microbial consortia are ubiquitous in nature and are involved in a number of processes of significant relevance to humans, including wastewater treatment, environmental remediation and assistance in food digestion. There is significant interest in developing synthetic microbial consortia because they can carry out complex tasks that individual organisms cannot and are more tolerant to environmental fluctuations (Brenner et al., *Trends Biotechnol* 26(9):483-489, 2008).

SUMMARY

The present disclosure discloses self-sustained, safe, stable and scalable microbial consortia (S$^5$MicroCon). The microbial consortia are regulated by photoautotroph-heterotroph interactions and RNA aptamer-based gene circuits. Also disclosed is a rapid, high-throughput method for engineering riboswitches that can be used, for example, in conjunction with the microbial consortia.

Provided herein are isolated microbial consortia that include (1) a driver module that provides a source of carbon and oxygen to the consortium; (2) a process module that carries out the function of the consortium; and (3) a control module that senses the integrity and functional output of the consortium.

In some embodiments, the driver module includes at least one photoautotrophic microorganism comprising a first driver module nucleic acid construct that directs constitutive expression of an encoded toxin; and a second driver module nucleic acid construct encoding a corresponding antitoxin, wherein expression of the antitoxin is regulated by a riboswitch responsive to a signaling molecule produced by the control module.

In some embodiments, the process module includes at least one heterotrophic microorganism comprising a first process module nucleic acid construct encoding a functional protein, wherein expression of the functional protein is regulated by a riboswitch responsive to an exogenous molecule; and a second process module nucleic acid construct encoding a process module-specific signaling molecule.

In some embodiments, the control module includes a first control module nucleic acid construct encoding a control module-specific signaling molecule, wherein expression of the control module-specific signaling molecule is regulated by the process module-specific signaling molecule.

Also provided are kits that include a microbial consortium disclosed herein. In some embodiments, the kits further include growth media and/or a culture vessel.

Further provided is a method for selecting a functional riboswitch responding to a selected ligand. In some embodiments, the method includes cloning an RNA aptamer that specifically binds the ligand upstream of a random nucleic acid sequence having a length of 12-30 nucleotides and which is operably linked to a selectable marker gene, thereby producing a library of candidate riboswitch sequences; transforming bacteria with the library to produce a transformed culture of bacteria; dividing the transformed culture of bacteria into a first culture grown in the presence of the ligand and a second culture grown in the absence of the ligand, wherein both cultures are grown in the presence of a selection pressure; isolating the candidate riboswitch sequences from the first culture and the second culture; sequencing the candidate riboswitch sequences from the first culture and the second culture; and selecting putative functional riboswitches, which are riboswitch sequences that are more abundant in the first culture compared to the second culture.

Also provided is a method for generating and selecting a functional riboswitch responsive to a selected ligand. In some embodiments, the method includes providing a library of random RNA molecules 50-100 nucleotides in length; providing a column comprising the selected ligand immobilized to a solid support; contacting the column with the random RNA molecules, whereby any RNA molecules that specifically bind to the selected ligand are retained in the column; eluting the bound RNA molecules from the column to isolate ligand-binding RNAs; cloning the ligand-binding RNAs upstream of a random nucleic acid sequence having a length of 12-30 nucleotides and which is operably linked to a selectable marker gene, thereby producing a library of candidate riboswitch sequences; transforming bacteria with the library to produce a transformed culture of bacteria; dividing the transformed culture of bacteria into a first culture grown in the presence of the ligand and a second culture grown in the absence of the ligand, wherein both cultures are grown in the presence of a selection pressure; isolating the candidate riboswitch sequences from the first culture and the second culture; sequencing the candidate riboswitch sequences from the first culture and the second culture; and selecting functional riboswitches, which are riboswitch sequences that are more abundant in the first culture compared to the second culture.

The foregoing and other objects and features of the disclosure will become more apparent from the following detailed description, which proceeds with reference to the accompanying figures.

BRIEF DESCRIPTION OF THE DRAWINGS

FIG. 6A provides an overview of a microbial consortium, which includes a Driver module (1), a Process module (2) and a Control module (3). FIG. 6B depicts a Driver module that functions as the primary producer. FIG. 6C shows the Process module that facilitates the function (detection of THP in this example) of the microbial consortium. FIG. 6D depicts a Control module that serves as the sensor and actuator of the microbial consortium.

SEQUENCE LISTING

Figure 1:
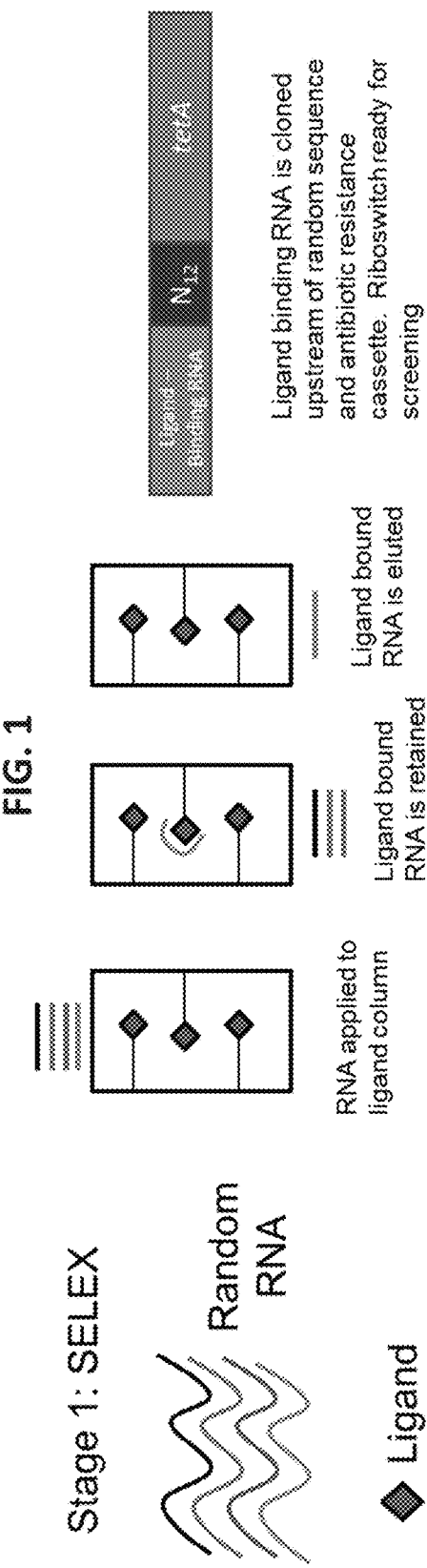
FIG. 1 is a schematic showing the process for the development of new riboswitches, which is based on selecting RNA transcripts that bind a ligand of choice, followed by enrichment and sequencing to identify functional riboswitch elements. In the first stage, random RNA is applied to a ligand column and any ligand bound to the RNA is retained in the column. Ligand-bound RNA is then eluted and cloned upstream of random sequence (e.g. $N_{12}$) and a bacteriostatic antibiotic resistance cassette (e.g. tetA), which provides a riboswitch library that is ready for screening. In the second stage, E. coli transformed with the riboswitch library is cultured with and without ligand and with a selection pressure (e.g. antibiotic corresponding to the resistance cassette used, tetracycline in this example). Bacteria with functional riboswitches are able to tolerate the selection pressure and become more abundant only when the ligand is present. This growth and replication also increases the abundance of the functional riboswitch itself and sequencing is carried out to identify those riboswitches that are more abundant in the presence of ligand, thereby identifying functional riboswitches (−Ligand=SEQ ID NOs: 1-8; +Ligand=SEQ ID NOs: 1, 5 and 8).
Figure 1:
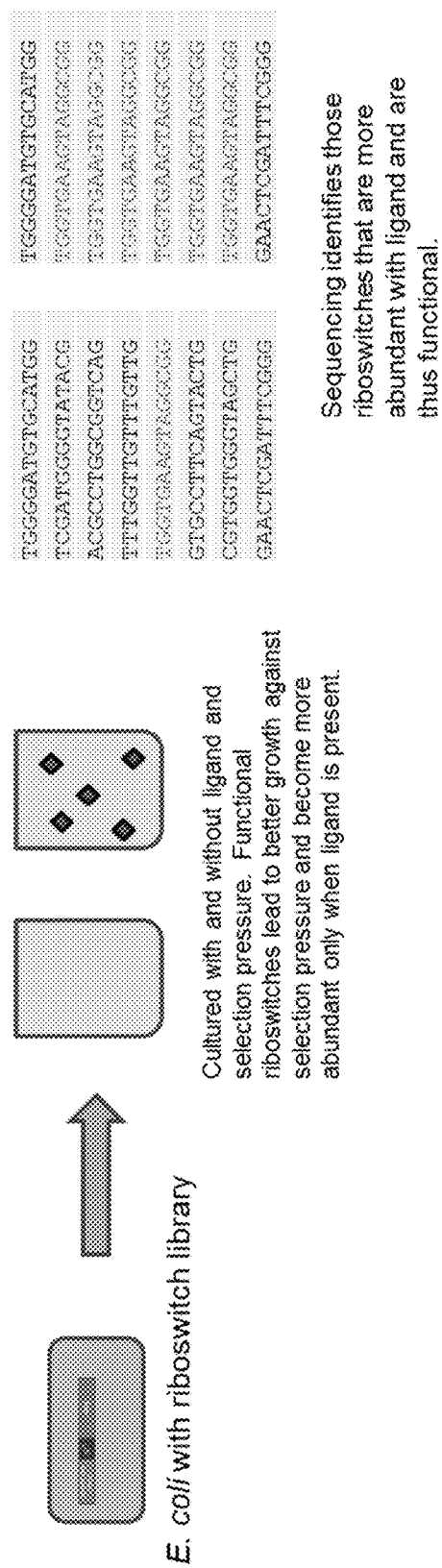

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 6, 2016, 12 KB, which is incorporated by reference herein. In the accompanying sequence listing:

SEQ ID NOs: 1-8 are nucleotide sequences of exemplary riboswitches.

SEQ ID NOs: 9-16 and 18-26 are nucleotide sequences of putative THP-responsive riboswitches.

SEQ ID NOs: 17 and 27 are nucleotide sequences of THP-responsive consensus riboswitches.

SEQ ID NO: 28 is the nucleotide sequence of a THP riboswitch.

SEQ ID NO: 29 is the nucleotide sequence of a pAF riboswitch.

SEQ ID NOs: 30-32 are nucleotide sequences of papA, papB and papC of the pAF operon, codon-optimized for expression in E. coli.

DETAILED DESCRIPTION

I. Abbreviations

AHL acyl homoserine lactone
bp base pair
NGS Next-Gen Sequencing
pAF p-amino-phenylalanine
S⁵MicroCon Self-Sustained, Safe, Stable, and Scalable Microbial Consortium
SELEX Systematic Evolution of Ligands by EXponential enrichment
THP theophylline II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Acyl homoserine lactones (AHLs): A class of signaling molecules involved in bacterial quorum sensing. AHLs are carboxamides consisting of a homoserine lactone having an unspecific N-acyl substitution. AHLs produced by different bacteria differ in the length of the R-group side chain. Chain lengths vary from 4 to 18 carbon atoms and in the substitution of a carbonyl at the third carbon. AHLs are also known as N-Acly homoserine lactones (N-AHLs).

Antibiotic resistance gene: A gene that renders a microorganism resistant to the effects of a particular antibiotic. Numerous antibiotic resistance genes are known in the art. Exemplary antibiotic resistance genes include, but are not limited to, β-lactamase (confers resistance to ampicillin), Neo (confers resistance to kanamycin and geneticin) and tetA (confers resistance to tetracycline).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Bioremediation: A waste management technique that utilizes organisms to remove or neutralize pollutants from a contaminated site. The organisms used for bioremediation can be naturally occurring organisms or genetically modified organisms.

Control module: One component of the microbial consortia disclosed herein. The control module includes a genetic element that is either contained within the Process module or is contained within a separate heterotrophic microorganism. The function of the Control module is to sense the integrity and monitor the functional output of the consortium. The genetic element of the Control module encodes a signaling molecule that regulates expression of an antitoxin in the Driver module via a riboswitch responsive to the signaling molecule. Expression of the Control module signaling molecule only occurs upon sensing one or more signaling molecules produced by the Process module.

Cyanobacteria: A phylum of bacteria that obtain their energy through photosynthesis. Cyanobacteria are photoautotrophic microorganisms. In some examples herein, the cyanobacteria is a species of *Synechococcus* (such as *Synechococcus* sp. PCC 7002, *S. ambiguous*, *S. arcuatus* var. *calcicolus*, *S. bigranulatus*, *S. brunneolus*, *S. caldarius*, *S. capitates*, *S. carcerarius*, *S. elongates*, *S. endogloeicus*, *S. epigloeicus*, *S. ferrunginosus*, *S. intermedius*, *S. koidzumii*, *S. lividus*, *S. marinus*, *S. minutissimus*, *S. mundulus*, *S. nidulans*, *S. rayssae*, *S. rhodobaktron*, *S. roseo-persicinus*, *S. roseo-purpureus*, *S. salinarum*, *S. salinus*, *S. sciophilus*, *S. sigmoideus*, *S. spongiarum*, *S. subsalsus*, *S. sulphuricus*, *S. vantieghemii*, *S. violaceus*, *S. viridissimus* or *S. vulcanus*), *Cyanothece* (such as *Cyanothece* sp. ATCC 51142, *C. aeruginosa*, *C. epiphytica*, *C. halobia*, *C. lineata*, *C. major* or *C. shiloi*), or *Synechocystis* (such as *Synechocystis* sp. PCC6803, *S. aquatillis*, *S. bourrellyi*, *S. buzasii*, *S. consortia*, *S. crassa*, *S. diplococca*, *S. endobiotica*, *S. endophytica*, *S. fuscopigmentosa*, *S. limnetica*, *S. major*, *S. minima*, *S. miniscula*, *S. parvula*, *S. pevalekii*, *S. planctonica*, *S. primigenia*, *S. sallensis*, *S. salina*, *S. septentrionalis*, *S. skujae*, *S. thermalis* or *S. trididemni*).

Driver module: One component of the microbial consortia disclosed herein. The Driver module includes at least one photoautotrophic microorganism that serves to produce oxygen and as a source of fixed carbon for the other two components of the consortia (the Process module and the Control module). The Driver module constitutively expresses a toxin and only expresses the corresponding antitoxin upon sensing a signaling molecule produced by the Control module. In some embodiments herein, the photoautotrophic microorganism(s) is a type of cyanobacteria. In other embodiments, the photoautotrophic microorganism(s) is a type of algae.

Enzyme: A protein that accelerates or catalyzes a chemical reaction.

Exogenous molecule: In the context of the present disclosure, an "exogenous molecule" is any molecule in the environment surrounding the microbial consortium. The exogenous molecule can be, for example, a small molecule, chemical or pathogenic organism, or component thereof, from the environment.

Fluorescent protein: A protein that emits light of a certain wavelength when exposed to a particular wavelength of light. Fluorescent proteins include, but are not limited to, green fluorescent proteins (such as GFP, EGFP, AcGFP1, Emerald, Superfolder GFP, Azami Green, mWasabi, TagGFP, TurboGFP and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyanl, Midori-Ishi Cyan, mTurquoise and mTFP1), yellow fluorescent proteins (EYFP, Topaz, Venus, mCitrine, YPet, TagYFP, PhiYFP, ZsYellowl and mBanana), orange fluorescent proteins (Kusabira Orange, Kusabira Orange2, mOrange, mOrange2 and mTangerine), red fluorescent proteins (mRuby, mApple, mStrawberry, AsRed2, mRFP1, JRed, mCherry, HcRed1, mRaspberry, dKeima-Tandem, HcRed-Tandem, mPlum, AQ143, tdTomato and E2-Crimson), orange/red fluorescence proteins (dTomato, dTomato-Tandem, TagRFP, TagRFP-T, DsRed, DsRed2, DsRed-Express (T1) and DsRed-Monomer) and modified versions thereof.

Functional protein: In the context of the present disclosure, a "functional" protein refers to a protein that is capable of carrying out a specific activity or function. In some embodiments, the functional protein is a reporter protein, such as a fluorescent protein, the function of which is to fluoresce to enable detection of the protein. In other embodiments, the functional protein is an enzyme that is capable of catalyzing a particular chemical reaction, such as a reaction that contributes to bioremediation.

Heterologous: A heterologous protein or polypeptide refers to a protein or polypeptide derived from a different source or species.

Heterotroph: An organism that derives its nutritional requirements from complex organic substances. In some examples herein, the heterotroph is *Escherichia coli* or a species of *Shewanella*.

Ligand: A molecule that binds to another molecule. In the context of the present disclosure, a "ligand" is a molecule that binds an RNA aptamer, such as the aptamer portion of a riboswitch. In some embodiments herein, the ligand is a small molecule. In specific examples, the ligand is THP or pAF.

Microbial consortium: A mixture, association, or assemblage of two or more microbial species, which in some instances are in physical contact with one another. The microbes in a consortium may affect one another by direct physical contact or through biochemical interactions, or both. For example, microbes in a consortium may exchange nutrients, metabolites, or gases with one another. Thus, at least some of the microbes in a consortium may be metabolically interdependent. Such interdependent interactions may change in character and extent through time and with changing culture conditions. Microbial consortia are generally involved in a common process or achieve a common outcome by combining their individual processes. In some embodiments herein, the microbial consortium includes at least two different organisms, including one phototrophic species and one heterotrophic species. In other embodiments, the microbial consortium includes at least three different organisms, including one phototrophic species and two heterotrophic species.

Microorganism: A microscopic organism. Microorganisms include, but are not limited to, bacteria, cyanobacteria, algae, fungi and protozoa. In some instances, microorganisms are single-cellular organisms (for example, bacteria, cyanobacteria, some fungi, or some algae). In other instances, the term microorganism includes multi-cellular organisms, such as certain fungi or algae (for example, multicellular filamentous fungi or multicellular algae). In some embodiments herein, the microorganism is a cyanobacterium or a heterotrophic bacterium, such as *E. coli*. Microorganisms are also known as microbes.

Nucleic acid construct: A nucleic acid molecule containing the components necessary to carry out expression of an encoded protein. In some embodiments, the nucleic acid construct comprises the coding sequence for a protein operably linked to a promoter. In some embodiments, the nucleic acid construct comprising a protein coding sequence operably linked to a riboswitch. In some examples, the nucleic acid construct comprises a plasmid.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

P-amino-phenylalanine (pAF): An alternative amino acid.

Photoautotroph: An organism that is able to use light as its sole source of energy, and carbon dioxide as its sole source of carbon. Algae, cyanobacteria and green plants are types of photoautotrophs. Photoautotrophs are also known as phototrophs. In some examples herein, the photoautotroph is a type of cyanobacteria.

Process module: One component of the microbial consortia disclosed herein. The Process module comprises one or more heterotrophic microorganisms and is responsible for carrying out the desired function of the consortium, such as, but not limited to, sensing (e.g., detecting or measuring the presence of) a chemical in the environment or bioremediation. To carry out the function of the consortium, the Process module encodes a functional protein (such as a reporter protein or enzyme), the expression of which is regulated by a riboswitch responsive to an exogenous molecule (such as a chemical or pathogenic organism, or component thereof, from the environment). The Process module also encodes a signaling molecule that regulates expression of the Control module signaling molecule. In some embodiments, the heterotrophic microorganism is *E. coli* or a species of *Shewanella*.

Recombinant: A recombinant nucleic acid molecule or protein is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids and proteins that have been altered solely by addition, substitution, or deletion of a portion of the natural nucleic acid molecule or protein.

Reporter protein: A protein that can be readily identified and/or measured. Reporter proteins include, for example, fluorescent proteins and enzymes (for example, enzymes that generate a detectable product).

Riboswitch: A regulatory segment of RNA that binds a ligand (such as a small molecule), resulting in a change (increase or decrease) in expression of the protein encoded by the RNA. The riboswitches disclosed herein include an RNA aptamer portion, which binds the ligand, a linker (such as a random nucleic acid sequence) and a protein coding region.

RNA aptamer: A small ribonucleic acid that specifically binds a target molecule.

Selectable marker: A gene introduced into a cell, such as a bacterial cell, that confers a trait suitable for artificial selection. Exemplary selectable markers include antibiotic resistance genes. Expression of an antibiotic resistance gene in a bacterial cell (for example) confers a selective advantage to the bacterial cell such that it can be grown in the presence of the antibiotic.

Selection pressure: In the context of microbial growth, a "selection pressure" is a particular growth condition or an agent that that allows for the selection of microorganisms that are resistant to the selection pressure. For example, antibiotics are a common selection pressure. Microorganisms encoding a gene that confers resistance to the antibiotic become more abundant in a culture (e.g., relative to microorganisms not encoding the gene that confers resistance to the antibiotic).

*Shewanella*: A genus of marine bacteria. *Shewanella* species are a normal component of the surface flora of fish. *Shewanella* species include, but are not limited to, *S. abyssi, S. algae, S. algidipiscicola, S. amazonensis, S. aquimarina, S. baltica, S. benthica, S. colwelliana, S. decolorationis, S. denitrificans, S. donghaensis, S. fidelis, S. frigidimarina, S. gaetbuli, S. gelidimarina, S. glacialipiscicola, S. hafniensis, S. halifaxensis, S. halitois, S. hanedai, S. irciniae, S. japonica, S. kaireitica, S. livingstonensis, S. loihica, S. marinintestina, S. marisflavi, S. morhuae, S. olleyana, S. oneidensis, S. pacifica, S. pealeana, S. piezotolerans, S. pneumatophore, S. profunda, S. psychrophila, S. putrefaciens, S. sairae, S. schegeliana, S. sediminis, S. spongiae, S. surugensis, S. violacea, S. waksmanii, S. woodyi*.

Signaling molecule: Any molecule capable of transmitting a signal to a nucleic acid construct (such as a riboswitch), a cell or an organism. Signaling molecules include, but are not limited to, small molecules, amino acids (including non-canonical and unnatural amino acids), peptides and proteins.

Small molecule: A molecule, typically with a molecular weight less than about 1000 Daltons, or in some embodiments, less than about 500 Daltons, wherein the molecule is capable of modulating, to some measurable extent, an activity of a target molecule.

Solid support: Any material having a rigid or semi-rigid surface. In the context of the present disclosure, the solid support is capable of binding directly or indirectly to a ligand. Exemplary solid supports include, but are not limited to, beads (such as agarose beads, SEPHAROSE™ beads, magnetic beads, cellulose beads and polystyrene beads), particles (such as microparticles), resins, gels, columns, membranes (such as nitrocellulose membranes and polyvinylidene difluoride (PVDF) membranes), plates (such as microtiter or multi-well plates), slides, glass and metal.

Synthetic: Produced by artificial means in a laboratory.

Theophylline (THP): A derivative of xanthine. THP is also known as 1,3-dimethylxanthine.

Toxin/antitoxin system: A set of two or more closely related genes that encode a protein toxin and a corresponding antitoxin. These systems can be found in a number of different bacteria and archaea. Toxin/antitoxin systems are typically classified according to how the antitoxin neutralizes the toxin. In type I systems, the translation of the mRNA that encodes the toxin is inhibited by the binding of a small non-coding RNA antitoxin to the mRNA. The protein toxin in Type II systems is inhibited post-translationally by the binding of a protein antitoxin. In a Type III toxin/antitoxin system, the protein toxin is bound and inhibited directly by an RNA molecule. In some embodiments herein, the toxin and antitoxin are encoded by a Type II system. In some examples, the toxins and antitoxins are encoded by genes found in *E. coli* or a species of cyanobacteria. In particular examples, the toxin and antitoxin proteins are respectively encoded by ccdB and ccdA; mazFa and mazEa; relEs and relN; or vapC and vapB; mazE; gef and sof; yafO and yafN; or parE and parD.

Transform: To introduce a nucleic acid molecule into a cell, such as into a bacterial cell. Transformation of a cell can be carried out using any technique known in the art, such as by transfection or lipofection.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are self-sustained, safe, stable and scalable microbial consortia (S$^5$MicroCon). The microbial consortia are regulated by photoautotroph-heterotroph interactions and RNA aptamer-based gene circuits (riboswitches). Also disclosed herein are rapid, high-throughput methods for engineering RNA aptamer-based gene circuits, such as riboswitches that can be utilized in the disclosed microbial consortia.

The present disclosure provides isolated microbial consortia that include (1) a driver module that provides a source of carbon and oxygen to the consortium; (2) a process module that carries out the function of the consortium; and (3) a control module that senses the integrity and functional output of the consortium.

In some embodiments, the driver module comprises at least one photoautotrophic microorganism. The photoautotrophic microorganism(s) includes a first driver module nucleic acid construct that directs constitutive expression of an encoded toxin; and a second driver module nucleic acid construct encoding a corresponding antitoxin. Expression of the antitoxin is regulated by a ribo switch responsive to a signaling molecule produced by the control module.

In some examples, the photoautotrophic microorganism of the driver module includes a species of cyanobacteria. In particular examples, the cyanobacteria is a species of *Synechococcus*, *Cyanothece* or *Synechocystis*. In specific non-limiting examples, the cyanobacteria includes *Synechococcus* sp. PCC 7002, *Cyanothece* sp. ATCC 51142, or *Synechocystis* sp. PCC6803.

In some examples, the driver module toxin and antitoxin are respectively encoded by ccdB and ccdA; mazFa and mazEa; relEs and relN; or mapC and vapB. However, any toxin/antitoxin pair suitable for expression in the selected species of cyanobacterium can be used.

In some embodiments, the process module includes at least one heterotrophic microorganism, such as one, two, three or four heterotrophic microorganisms. The heterotrophic organism(s) comprises a first process module nucleic acid construct encoding a functional protein, wherein expression of the functional protein is regulated by a riboswitch responsive to an exogenous molecule; and a second process module nucleic acid construct encoding a process module-specific signaling molecule.

In some examples, the at least one heterotrophic microorganism of the process module comprises *Escherichia coli* and/or a species of *Shewanella*. In particular examples, the *Shewanella* species is *Shewanella putrefaciens* W3-18-1.

The functional protein expressed by the process module can be any type of protein that is capable of carrying out some type of function, such as providing a detectable signal or carrying out a specific reaction. In some examples, the functional protein is a fluorescent protein, or another protein that provides a visible readout. In other examples, the protein is an enzyme that carries out a specific reaction.

The exogenous molecule detected by the process module can be any type of molecule one has a desire to detect, such as a chemical or pathogenic organism (or component thereof) in the environment. A riboswitch responsive to the exogenous molecule can be engineered using the methods disclosed herein. In some embodiments, the exogenous molecule is a small molecule, a chemical or an antigen. In one example disclosed herein, the exogenous molecule comprises theophylline (THP).

In some embodiments disclosed herein, the process module-specific signaling molecule includes an acyl homoserine lactone (AHL). In other embodiments, the process module-specific signaling molecule comprises an alternative/unnatural amino acid or a small signaling peptide. A riboswitch responsive to the selected signaling molecule can be generated using the methods disclosed herein.

In some embodiments of the microbial consortia, the process module further includes a third process module nucleic acid construct that drives constitutive expression of an encoded toxin; and a fourth process module nucleic acid construct encoding a corresponding antitoxin. Expression of the antitoxin is regulated by a riboswitch responsive to the process module-specific signaling molecule. In some examples, the process module toxin and antitoxin are respectively encoded by ccdB and ccdA; mazF and mazE; gef and sof; yafO and yafN; or parE and parD. However, any toxin/antitoxin pair suitable for expression in the selected heterotrophic species can be used.

In some embodiments, the control module includes a first control module nucleic acid construct encoding a control module-specific signaling molecule. Expression of the control module-specific signaling molecule is regulated by a riboswitch responsive to the process module-specific signaling molecule. In some instances, the control module is contained within the process module (for example, the at least one heterotrophic microorganisms of the process module are transformed with the first control module nucleic acid construct). In other instances, the control module is a separate heterotrophic species that includes the first control module nucleic acid construct.

In some examples, the control module-specific signaling molecule includes p-amino-phenylalanine (pAF). In other examples, the control module-specific signaling molecule includes a different unnatural amino acid or a small signaling peptide. A riboswitch responsive to the selected signaling molecule can be generated using the methods disclosed herein.

In some embodiments of the microbial consortia, the control module further includes a second control module nucleic acid construct that drives constitutive expression of an encoded toxin; and a third control module nucleic acid construct encoding a corresponding antitoxin. Expression of the antitoxin is regulated by a riboswitch responsive to the control module-specific signaling molecule. In some examples, the control module toxin and antitoxin are respectively encoded by ccdB and ccdA; mazF and mazE; gef and sof; yafO and yafN; or parE and parD. However, any toxin/antitoxin pair suitable for expression in the selected heterotrophic species can be used.

Also provided by the present disclosure are kits that include a microbial consortium disclosed herein. In some embodiments, the kits further include appropriate growth media and/or a culture vessel. Methods for the co-culture of photoautotrophs and heterotrophs have been previously described (see, for example, U.S. Pat. No. 8,518,690, which is herein incorporated by reference). In some examples, the culture vessel is a closed reactor vessel. In some examples, the growth media comprises A+ medium containing the following components: Tris (8.255 mM), $Na_2EDTA$ (0.0806 mM), KCl (8.0483 mM), $CaCl_2*2H_2O$ (1.8120 mM), $MgSO_4*7H_2O$ (20.2860 mM), $KH_2PO_4$ (0.3670 mM), NaCl (308.0082 mM), $NH_4Cl$ (11.7540 mM-20.0 mM), Vitamin B12 ($2.95 \times 10^{-6}$ mM), $H_3BO_3$ (0.5547 mM), $MnCl_2*4H_2O$ (0.0218 mM), $ZnCl_2$ (0.0023 mM), $CoCl_2*6 H_2O$ (0.00018 mM), $Na_2MoO_4*2H_2O$ (0.00018 mM), $CuSO_4*5H_2O$ (0.000012 mM).

The microbial consortia disclosed herein can be used for any number of different purposes. For example, the microbial consortia can be used for biosensing of exogenous chemicals and/or intermediates and degradation products; biosensing of pathogenic organisms or their molecular signatures; biochemical synthesis including, but not limited to, precursors of hydrocarbon fuels, hydrogen, amino acids, organic acids, alcohols, fertilizers an nutraceuticals; bioremediation of wastewater and soils; or resource recovery of low-solubility minerals, such as metal ores and phosphates.

Further provided herein are methods for selecting a functional riboswitch to a selected ligand. In some embodiments, the method includes cloning an RNA aptamer that specifically binds the ligand upstream of a random nucleic acid sequence having a length of 12-30 nucleotides and which is operably linked to a selectable marker gene, thereby producing a library of candidate riboswitch sequences; transforming bacteria with the library to produce a transformed culture of bacteria; dividing the transformed culture of bacteria into a first culture grown in the presence of the ligand and a second culture grown in the absence of the ligand, wherein both cultures are grown in the presence of a selection pressure; isolating the candidate riboswitch sequences from the first culture and the second culture; sequencing the candidate riboswitch sequences from the first culture and the second culture; and selecting functional riboswitches, which are riboswitch sequences that are more abundant in the first culture compared to the second culture.

In some examples, the random nucleic acid sequence has a length of 15-25, 15-22, 18-25, or 22-24 nucleotides in length. In non-limiting examples, the random nucleic acid sequence has a length of 12, 13, 14, 15, 16, 17, 18, 19, 20, 21, 22, 23, 24, 25, 26, 27, 28, 29 or 30 nucleotides in length.

In some examples, the selectable marker gene comprises an antibiotic resistance gene, such as tetA.

In some examples, the bacteria are *E. coli*.

Also provided is a method for generating and selecting a functional riboswitch responsive to a selected ligand. In some embodiments, the method includes providing a library of random RNA molecules 50-100 nucleotides in length; providing a column comprising the selected ligand immobilized to a solid support; contacting the column with the random RNA molecules, whereby any RNA molecules that specifically bind to the selected ligand are retained in the column; eluting the bound RNA molecules from the column to isolate ligand-binding RNAs; cloning the ligand-binding RNAs upstream of a random nucleic acid sequence having a length of 12-30 nucleotides and which is operably linked to a selectable marker gene, thereby producing a library of candidate riboswitch sequences; transforming bacteria with the library to produce a transformed culture of bacteria; dividing the transformed culture of bacteria into a first culture grown in the presence of the ligand and a second culture grown in the absence of the ligand, wherein both cultures are grown in the presence of a selection pressure; isolating the candidate riboswitch sequences from the first culture and the second culture; sequencing the candidate riboswitch sequences from the first culture and the second culture; and selecting functional riboswitches, which are riboswitch sequences that are more abundant in the first culture compared to the second culture.

In some examples, the random RNA molecules 50-100 nucleotides in length are either a straight run of random nucleotides or they are split into two sequences of random nucleotides (for example, 25-50 nucleotides in length flanking a 12 nucleotide stem-loop structure). In specific examples, the random RNA molecules are 60-90 or 70-80 nucleotides in length. In non-limiting examples, the random RNA molecules are about 50, about 55, about 60, about 65, about 70, about 75, about 80, about 85, about 90, about 95 or about 100 nucleotides in length.

In some examples, the solid support comprises agarose beads or SEPHAROSE™ beads.

In some examples, the random nucleic acid sequence has a length of 15-25, 15-22, 18-25, or 22-24 nucleotides in length. In non-limiting examples, the random nucleic acid sequence has a length of 12, 13, 14, 15, 16, 17, 18, 19, 20, 21, 22, 23, 24, 25, 26, 27, 28, 29 or 30 nucleotides in length.

In some examples, the selectable marker gene comprises an antibiotic resistance gene, such as tetA.

In some examples, the bacteria are E. coli.

IV. RNA Aptamer-Based Gene Circuits

The ability to precisely and accurately control genetic circuits has implications for the engineering of robust and safe microbial systems with desired outputs, such as the $S^5$MicroCon described herein. Disclosed herein is the development of a scalable and generalizable pipeline for the engineering and testing of functional genetic circuits (riboswitches) responding to specific target ligands using RNA-based devices. RNA-encoded control elements, such as riboswitches and ribozymes, act in a ligand-dependent manner and are composed of an RNA aptamer domain that senses and binds ligands, and a transducer module that undergoes conformational changes and controls gene expression via diverse control mechanisms such as transcription termination, translation inhibition, RNA splicing, RNA interference or RNA degradation. The modularity of these elements allows for engineering synthetic systems through designing aptamer sequences that sense (e.g., are specific for) a wide range of ligands and control the expression output in a dose-dependent manner. Disclosed herein is a new methodology to build novel riboswitches based on first selecting RNA transcripts that bind the ligand of choice followed by enrichment and sequencing to identify functional riboswitch elements (FIG. 1).

The pipeline approach disclosed herein is applicable to the development of many new riboswitches and aptamers. Methods commonly employed to identify riboswitches are based on manual screening of aptamer/switch pairs with functionality of riboswitches usually being detected via expression of a readout gene (e.g., antibiotic resistance, fluorescence protein, or β-galactosidase production). While this method's utility has been demonstrated through the development of several functional riboswitches, it is limited in how many aptamer/switch pairs can be screened in a given time frame. This is complicated by the fact that all methods for new riboswitch identification must contend with the fact that reporter expression can occur independently of ligand concentration. Reports of false switches that are constitutively "ON" can vary, but in all cases a large number of aptamer/switch pairs will not "switch" in response to the presence of the desired ligand and will always drive expression of the downstream gene.

Disclosed herein is a new generalizable framework for in vivo engineering of RNA-aptamer based circuits using directional selection, Next-Gen deep sequencing (NGS), and iterative computational analysis and optimization. The approach disclosed herein in some examples is characterized by several features, including one or more of: (i) makes use of a readout gene that allows for the selection of aptamer/switch pairs that both induce or repress expression of the downstream gene; (ii) employs a turbidostat system to allow for the addition or removal of reagents to a continuously-cultivated library of putative riboswitches; (iii) combines selection and enrichment of functional riboswitches into one in vivo step, simplifying identification; and (iv) uses NGS and computational analysis to identify a large number of functional riboswitches.

The pipeline described herein is divided into two stages with Stage I involving the isolation and enrichment of specific RNA sequences (aptamers) that bind to a ligand of choice. To carry this out, any suitable technique for identifying and selecting for ligand-binding RNA sequences can be used. As one example, SELEX (Systematic Evolution of Ligands by EXponential enrichment) can be used to enrich randomly designed RNA sequence libraries for those RNA molecules that specifically bind the ligand of choice. Briefly, the target ligands are immobilized onto a solid support (such as inert SEPHAROSE™ beads). In vitro transcribed random RNA sequences made from the chemically-synthesized combinatorial sequence library are passed over the column. RNAs that bind the target are selected and collected; competitive elutions are used to ensure that the selected RNAs bind with both high affinity and high specificity.

In Stage 2, the aptamers developed for a target ligand through SELEX are used to develop novel synthetic riboswitches driving the expression of a downstream gene only in the presence of the target ligand. While the sequences derived above bind to the ligand, a functional riboswitch needs to convey this binding state to a downstream gene and induce or repress expression of this gene accordingly. Therefore, aptamers developed as described above are linked to the downstream gene separated by a short sequence of random nucleotides to act as the "switch" portion. The downstream screening method acts to screen aptamer/switch pairs to identify those that form functional riboswitches.

Figure 3:
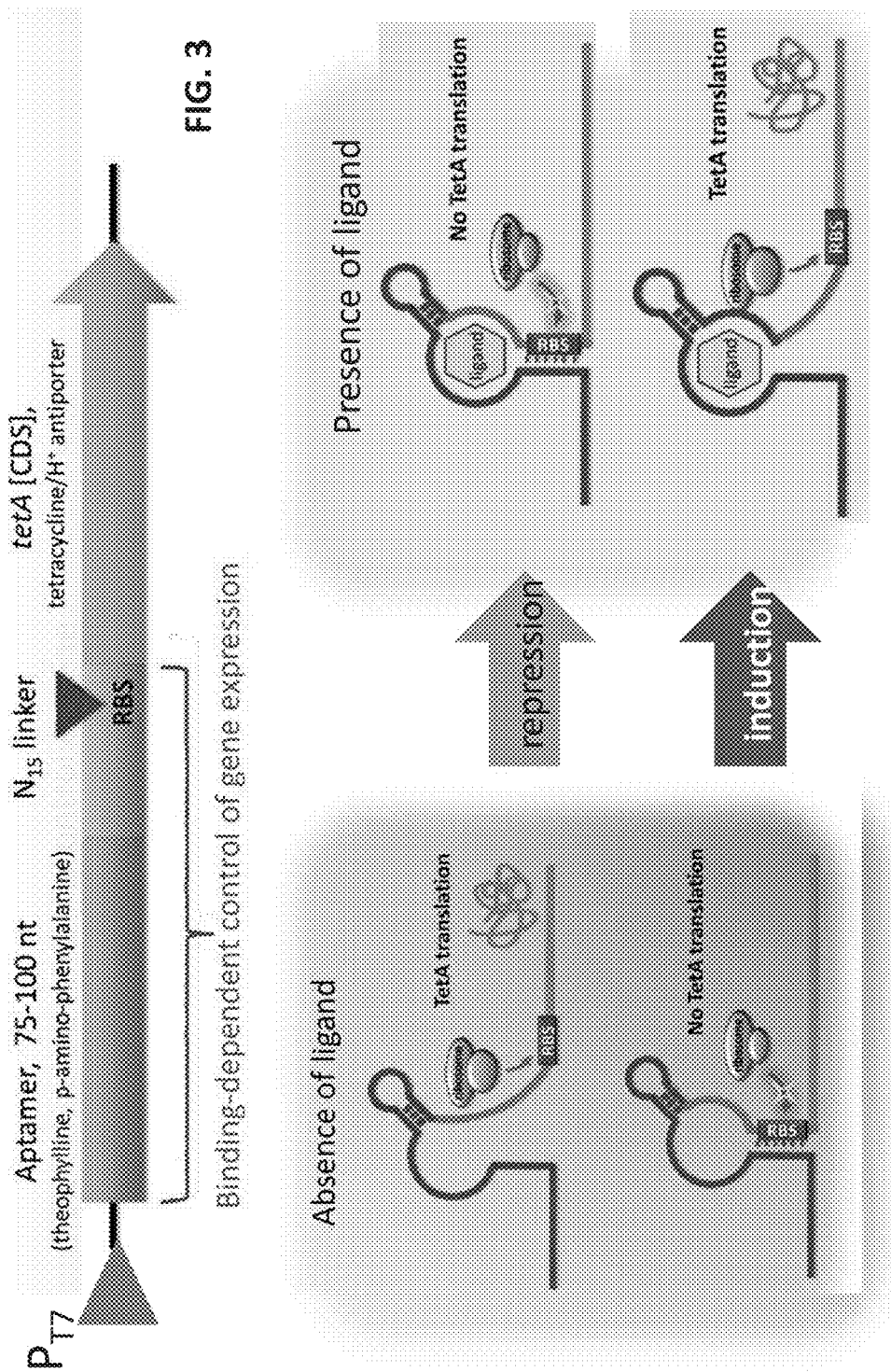
FIG. 3 shows a schematic of the general approach for the development of riboswitch-based gene circuits using an aptamer known to bind a particular ligand, such as theophylline or p-amino-phenylalanine. The aptamer sequence is cloned 5' of a random linker sequence (shown here as $N_{15}$) and an antibiotic resistance gene (such as tetA). Riboswitches that repress or induce expression of a downstream gene can be identified using this approach. Functional riboswitches that repress expression produce the downstream gene only in the absence of ligand, whereas functional riboswitches that induce expression produce the downstream gene only in the presence of ligand. Using an antibiotic resistance gene as the downstream gene allows for the selection and enrichment of functional riboswitches.
Figure 4:
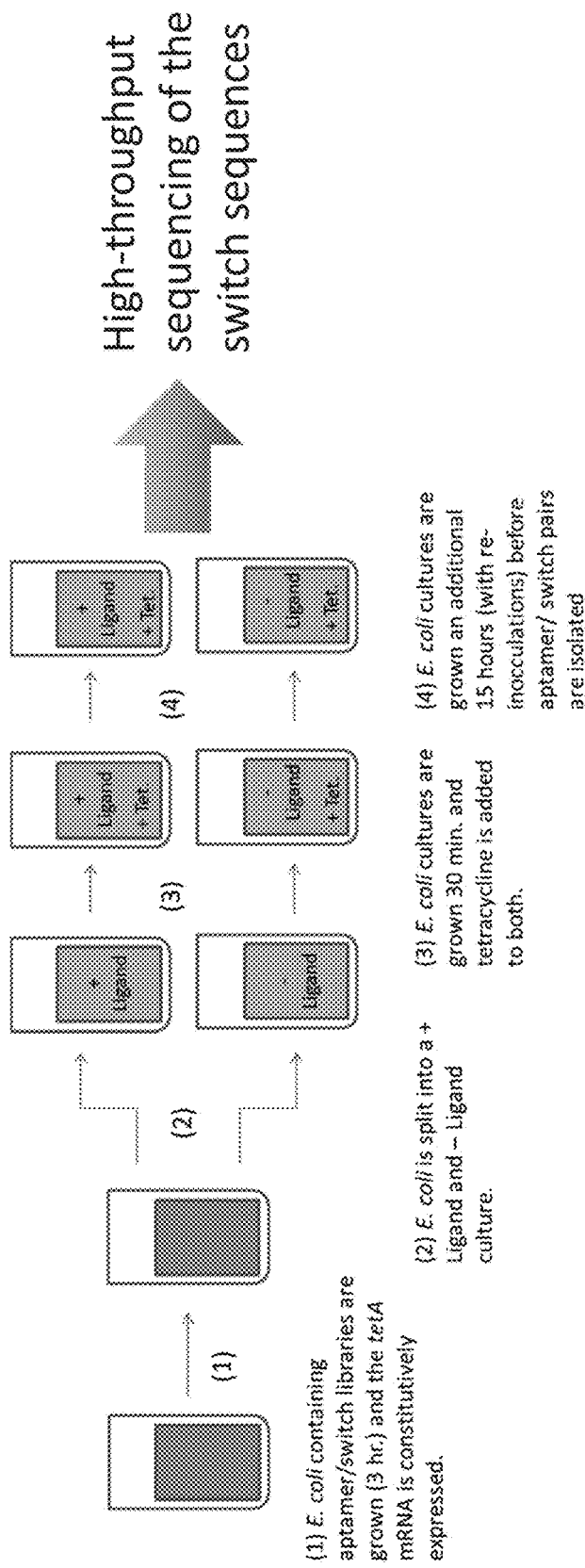
FIG. 4 is a schematic showing the details of process for selecting and enriching functional riboswitches. In this example, E. coli is transformed with a riboswitch library expressing tetA. The process includes the following steps: (1) E. coli containing the riboswitch libraries are cultured for approximately 3 hours; these bacteria express tetA mRNA constitutively but TetA protein production is a function of the riboswitch sequence. (2) The E. coli culture is split into +Ligand and −Ligand cultures. (3) After growth for 30 minutes, tetracycline is added to the E. coli cultures. (4) The cultures are grown for additional 15 hours before aptamer/switch pairs are isolated and subjected to high-throughput sequencing.

The pipeline is designed to link bacterial viability to selection of functional riboswitches. Riboswitches that repress or induce expression of a downstream gene can be identified using the approach disclosed herein (see FIG. 3 and FIG. 4). In one example, the tetracycline resistance marker, tetA, is used as the downstream gene. Libraries are cultured in duplicate either in the presence or absence of the ligand used in SELEX to induce expression of the TetA protein, followed by addition of tetracycline to both cultures. This induces an increase in abundance of bacteria harboring a successful riboswitch in cultures containing the ligand. Non-functional riboswitches either fail to grow or do not show a difference in abundance when the ligand is present or absent. These methods are generally carried out using various concentrations of the target ligand and various incubation times as less information is typically known regarding the cell permeability of the target ligand in vivo and the kinetics of the putative riboswitches. Plasmid DNA (containing the screened riboswitches) is then extracted from these cells and optionally stored. The final step in isolating functional riboswitches involves the sequencing of these plasmids to determine the sequence of aptamer/switch pairs. Riboswitch sequences that show a significantly higher abundance in the culture containing the ligand represent putative functional riboswitches that respond to ligand presence and induce expression of TetA.

Alternatively, functional riboswitches are identified by taking advantage of a negative selection protocol employing fusaric acid. In this method, constitutively "on" aptamers are eliminated from the pool by counter selecting with fusaric acid in the absence of tetracycline, as fusaric acid is lethal to organisms expressing TetA. Consequently, those organisms that produce TetA when the ligand is absent will be repressed by fusaric acid counterselection. Fusaric acid is then removed from the system followed by the addition of the ligand and tetracycline. Riboswitches that do not express TetA in response to the presence of the ligand are selected against, leaving only positive functional riboswitches (those that express TetA only in the presence of the ligand).

Figure 2:
FIG. 2 shows putative theophylline (THP)-responsive riboswitches. Sequencing of THP-responsive riboswitches identified approximately 1700 unique switch sequences that were screened with and without THP. Of these, 103 sequences were at least 2-fold more abundant when THP was present compared to when THP was absent. Similar sequences from the enrichment data were scanned with MEME to identify consensus riboswitch patterns. Two different riboswitch consensus sequences are shown (left, SEQ ID NO: 17; right, SEQ ID NO: 27).

An enrichment of this type has been carried out (see Example 1) and the data obtained demonstrates the feasibility of this approach. Two aptamers were used—one that had previously been shown to respond to theophylline (THP) and one that is responsive to p-amino-phenylalanine (pAF). Each aptamer was separated from the tetA gene with a 15 bp random sequence to act as the new "switch" portion. Screening and enrichment were carried out as described above. As the aptamer portion was identical in each library, only the 15 bp switch portion was examined. When examining THP-responsive riboswitches, sequencing identified approximately 1700 unique switch sequences (screened with and without THP). Of these, 103 showed at least 2-fold higher abundance when THP was present compared to when THP was absent. Some riboswitches showed greater than a 25-fold change in abundance as a function of THP presence. Several of these riboswitches had similar sequences, suggesting that minor modifications of the same riboswitch are being enriched concurrently (FIG. 2). A similar approach with pAF-responsive riboswitches sequenced approximately 2800 switch sequences and identified 105 that showed at least 2-fold higher abundance in the presence of pAF compared to the absence of pAF.

The approach disclosed herein is designed to isolate a small library of aptamer/switch pairs that lead to functional riboswitches, which are then identified through sequencing. In some instances, sequencing may give a very large number of putative riboswitches. As it is unlikely that all sequenced riboswitches will function with identical kinetics, there could be little indication as to which would be the best candidates for downstream study. If this is the case, Stage 2 can be repeated and only those riboswitches that are enriched in several independent rounds of directed evolution are selected for downstream study. The use of conventional cloning techniques combined with a relatively fast (2-3 day) enrichment approach means that multiple sets of putative riboswitches can be quickly and easily isolated, allowing for the luxury of choosing only the highest performing riboswitches (those that appear in several independent enrichments) for detailed study.

While the exemplary enrichment approach described in Example 1 uses tetA as a readout gene, the process disclosed herein allows for the development of modular riboswitches that can be used to induce the expression of any downstream gene. It is possible that riboswitches that drive the expression of one gene, such as tetA, may not function with other genes, possibly due to nucleotide sequences at the 5' end of the coding region that interfere with interaction of the aptamer and ribosome binding site. If this is the case, a longer random nucleotide sequence (e.g. longer than 15 nucleotides) can be introduced. In the exemplary studies disclosed herein, a random sequence of 15 nucleotides was used as this has worked well generating other riboswitches. However, the length of the random sequence could be expanded or reduced depending on need, thereby increasing or decreasing the physical separation of the ATG start codon in the readout gene and the aptamer portion/ribosome binding site (RBS) portion of the riboswitch.

V. Self-Sustained, Safe, Stable, Scalable, Microbial Consortium $S^5$MicroCon (Self-Sustained, Safe, Stable, and Scalable Microbial Consortium) represents a general engineering framework that can be used for designing and building consortia of microorganisms that require only sunlight and water as energy (reductant) sources to carry out a practical function in a safe, stable and scalable manner. The $S^5$MicroCon is unique in that it: (i) presents a new, compartmentalized, division-of-labor design for maintaining stability, resilience, and safety of microbial consortia; (ii) has built-in regulatory switches and feedback loops for self-control and adaptability to environmental fluctuations; (iii) contains a photoautotrophic input source, by which sunlight and atmospheric $CO_2$ serve as the sole source of energy and carbon for the communities; and (iv) provides flexibility to integrate interchangeable modules with various functional outputs using a plug-and-play framework based upon photoautotroph-heterotroph interactions. The disclosed $S^5$MicroCon can act as a stand-alone unit capable of operating safely within unpredictable and dynamic natural environments.

Figure 5:
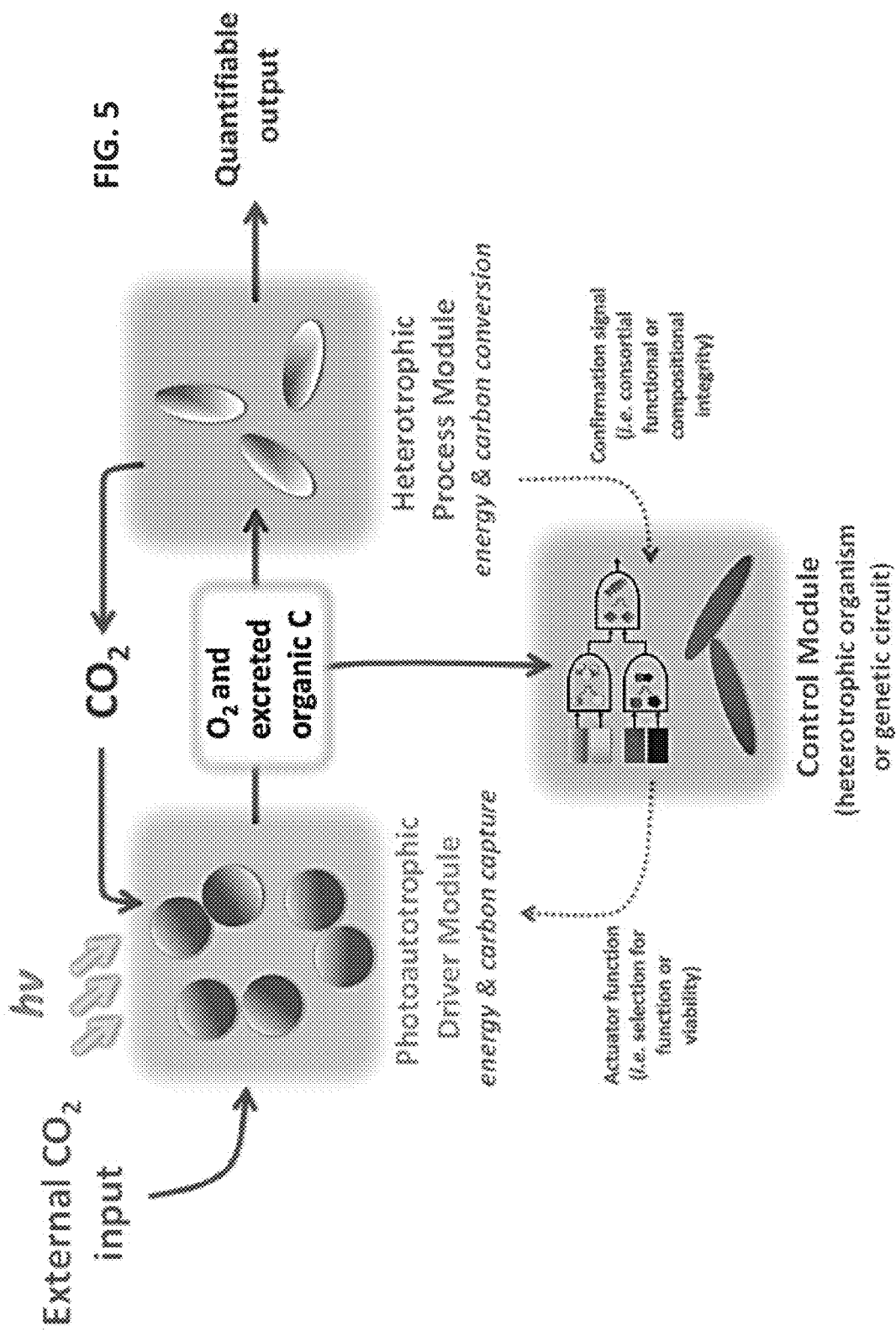
FIG. 5 provides a schematic overview of the S⁵MicroCon. The S⁵MicroCon is composed of three modules: a Driver module (e.g., a cyanobacterium that provides energy to the system in the form of reduced carbon), a Process module that carries out the desired function, and a Control module that senses Process module activity and controls the Drive module in response.

Photoautotroph-heterotroph associations are common in nature as they provide key ecosystem services such as carbon, nutrient, and metal cycling. Engineering co-culture systems can create opportunities for a well-defined, robust experimental system that demonstrates metabolic interdependency, and for which both members are amenable to genetic manipulation and systems-level analysis. By using photosynthetic strains that excrete organic carbon compounds (organic acids or sugars) that can be utilized by a heterotrophic partner growing in co-culture, the system can be supported with an external input of only light and atmospheric $CO_2$. The $S^5$MicroCon concept is based upon an engineering scheme for feedback-controlled biocatalyst composites consisting of three major components: driver, processor, and controller (FIG. 5). The driver module is a photoautotrophic organism (or more than one photoautotrophic organism) supporting the heterotrophic microbes in the process and/or control modules. Using an automated photobioreactor system, the ability of fast-growing cyanobacteria (e.g., *Synechococcus* PCC7002) to support the growth of heterotrophs, such as *E. coli* and *Shewanella* species, has been demonstrated. For initial studies, *Synechococcus* 7002 was selected as the driver module in the $S^5$MicroCon. The process module includes interchangeable heterotrophic organisms or consortia which utilize dissolved organic carbon secreted by the cyanobacterium as the sole source of carbon and energy. As one example, the Process module can be represented by a consortium of *E. coli* and *Shewanella* species. Finally, the control module includes either a discrete organism and/or a tunable genetic element (regulatory circuit) integrated into the system to sense both the community integrity and functional output of the entire process. The latter is programmable to impose a selection pressure on the Driver module based on chemical and/or physiological inputs. Only when all three modules are metabolically active can the whole consortium function. Each element is interdependent upon the others and performs a function essential to system integrity. This allows for a stable, robust, and safe microbial consortia that can be specifically tuned to perform a variety of processes such as, but not limited to, (1) biosensing of exogenous chemicals and/or intermediates and degradation products; (2) biosensing of pathogenic organisms or their molecular signatures; (3) biochemical synthesis, including precursors of hydrocarbon fuels, hydrogen, amino acids, organic acids, alcohols, fertilizers and nutraceuticals; (4) bioremediation of wastewater and soils; and (5) resource recovery of low-solubility minerals, such as metal ores and phosphates.

A. The Driver Module

The Driver module includes photoautotrophic organism (s) such as cyanobacteria or algae, for example *Synechococcus* species PCC 7002, that can take input energy (in the form of light) and carbon (in the form of $CO_2$ or $—HCO_3$) and convert it to reduced carbon sources that can be used by the Process and Control modules. The Driver module also produces $O_2$ for respiration use by the Process and Control modules and remove waste $CO_2$ produced by the species in both of these modules. Because all modules are interdependent, the Driver module depends on a signaling molecule that can only be expressed by the Control module, which will express it only upon receipt of an additional molecular signal from the Process module. Species in the Driver module contain a toxin-antitoxin pair, such as, but not limited to, ccdAB. The toxin, ccdB, is expressed constitutively, but the antitoxin is only expressed when the Control module-derived signaling molecule is present. This control of expression is mediated by either a riboswitch or DNA binding transcription factor that is designed to respond to the molecule. Generation of riboswitches is described above. Signaling molecules are chosen based on their small size and permeability to induce robust uptake by the cyanobacteria of the Driver module. For example, the alternative amino acid p-amino-phenylalanine (pAF), for which riboswitches have already been constructed, can be used.

B. The Process Module

The Process module carries out the desired function of the S$^5$MicroCon and is composed of one or more heterotrophic species. These heterotrophic species are non-competitive and niche-specific for carbon sources produced by the Driver module. For example, the Process module of the S$^5$MicroCon can contain a theophylline-responsive riboswitch driving the expression of soluble green fluorescent protein (sGFP). As noted above, communication between modules is required for the stability of this consortium. Therefore, each species of the Process module produces a unique signaling molecule that can be sensed by the Control module, such as two acyl homoserine lactones (AHLs), molecules often employed in microbial quorum sensing. Upon receipt of this signal, the Control module expresses the signaling molecule to be sensed by the Driver module (pAF in the above example). In addition to signaling the Control module, the AHL molecules act as activators of transcription factors in species of the Process module. Production of each of these molecules is used to trigger the expression of the the antitoxin ccdA of the ccdAB toxin-antitoxin pair. The toxin gene, ccdB, is expressed constitutively, similar to the Driver module described above. In this way, the Process module is able to signal to the Control module that it is metabolically active and abundant. If this signaling breaks down in the Process module, then the antitoxin is no longer made and the Process module shuts down.

C. The Control Module

The Control module includes additional heterotrophic species, for example E. coli, that act to stabilize the system through a continous production of a signaling molecule to be sensed by the Driver module. This expression takes place only when either or both of the AHL molecules produced by the Process module are sensed by the Control module. If there is an interruption in this communication, the Control module ceases production of the signaling molecule. This stops production of the antitoxin CcdA in the Driver module, which causes the death of the Driver module cyanobacterium. The loss of the Driver module leads to the loss of both the Process and Control modules as they depend on the Driver module for a source of reduced carbon. In some embodiments, the Control module is required to sense both of the AHL molecules from each of the two species of the Process module. In other embodiments, a signal from only a single species of the Process module is required. As with the Driver module, the viability of the Control module itself is dependent on the production of the signaling molecule (such as pAF in the above example) using the ccdAB system described above.

D. S$^5$MicroCon Modifications

The S$^5$MicroCon is a self-sufficient, stable and scalable consortium of bacterial species that can be designed to carry out a number of different functions. Although exemplary approaches are disclosed herein, several alternatives could be incorporated into the S$^5$MicroCon to either alter its function to a desired outcome or to alter the stability and scalability. For example, as an additional method to increase function and stability of the Process module, as well as gain additional knowledge regarding niche partitioning of cyanobacterial-heterotrophic communities, engineered strains of Synechococcus 7002 secreting increased amounts of sugars can be used. Synechococcus 7002 strains are generated containing transgenes driving expression and transport of lactate, fructose, glucose or sucrose using previously described methods. Synthesis of sugars by Synechococcus 7002 is further induced through culturing the S$^5$MicroCon in a high-salt medium. Use of a high salt medium combined with engineered strains of Synechococcus 7002 allows for the maximum production of sugars by these organisms, thereby driving metabolic activity and function of the Process and Control modules. Detailed knowledge regarding how heterotrophic species respond to varying sugar concentrations can be examined through altering salt content (and therefore sugar production) or through comparisons between S$^5$MicroCon containing engineered, sugar-producing Synechococcus 7002 and those containing wild-type strains.

The following examples are provided to illustrate certain particular features and/or embodiments. These examples should not be construed to limit the disclosure to the particular features or embodiments described.

EXAMPLES

Example 1

Engineering of THP- and pAF-Responsive Riboswitches

This example describes the development of two functional riboswitches that each include a previously described aptamer.

In this study, aptamers that had previously been shown to respond to either theophylline (THP) or p-amino-phenylalanine (pAF) were used. Each aptamer was separated from the tetA gene by a 15 base pair (bp) random sequence (which serves as the switch portion) to generate a riboswitch library. Screening and enrichment were performed as shown in FIG. 1 (Stage 2: Enrichment and Sequencing) and FIG. 4. E. coli cultures transformed with the riboswitch library were cultured in the presence and absence of ligand (THP or pAF); both cultures were grown in the presence of tetracycline as the selection pressure (i.e. +ligand/+tet and −ligand/+tet). E. coli containing functional riboswitches become more abundant in the cultures only when ligand is present (+ligand/+tet).

THP-responsive riboswitch sequencing identified approximately 1700 unique switch sequences that were screened with and without THP. Of these, 103 showed higher abundance (at least 2-fold) when THP was present compared to when THP was absent. Some riboswitches showed >25-fold change in abundance as a function of THP presence. Several of these riboswitches had similar sequences suggesting that minor modifications of the same riboswitch may be being enriched concurrently (FIG. 2). THP-responsive consensus riboswitch sequences are set forth herein as SEQ ID NOs: 17 and 27 (see also FIG. 2). pAF-responsive riboswitch sequencing identified approximately 2800 switch sequences, 105 of which showed at least 2-fold higher abundance in the presence of pAF compared to its absence. Exemplary THP-responsive and pAF-responsive riboswitch sequences are described in Example 2.

Example 2

Using Photoautotroph-Heterotroph Interactions as a Framework for Building Self-Sustained, Scalable Microbial Consortia Disclosed herein is the S⁵MicroCon platform that can be used to design and build consortia of microorganisms that require only sunlight and water as energy sources to carry out a desired function. An overview of the S⁵MicroCon platform is shown in FIG. 5. This platform is composed of three modules—the Driver module, the Process module and the Control module. The Driver module, which is typically a cyanobacterium, provides energy to the system in the form of reduced carbon. The Process module carries out the desired function of the consortium, and the Control module senses the activity of the Process module and the controls the Driver module in response.

The S⁵MicroCon platform is designed to act as a stand-alone unit capable of operating safely within unpredictable and dynamic natural environments. The functional outputs and interaction network between modules are programmed to be degenerate via synthetic regulatory circuitry. At the center of this synthetic community lies a photoautotroph-heterotroph interactive partnership. Such associations are ubiquitous in nature and mediate key ecological processes such as energy capture, carbon fixation and nutrient cycling. Genetically tractable photoautotrophic organisms, such as cyanobacteria, can sustain and drive an engineered consortium through production of $O_2$, organic carbon, and in some cases, fixed inorganic or organic nitrogen. This creates opportunities for metabolic engineering using interdependent multi-cellular modules self-sustained by generic aquatic environments. An exemplary self-sustained microbial consortium that can detect the presence of theophylline (THP) is depicted in FIGS. 6A-6D.

Figure 6A:
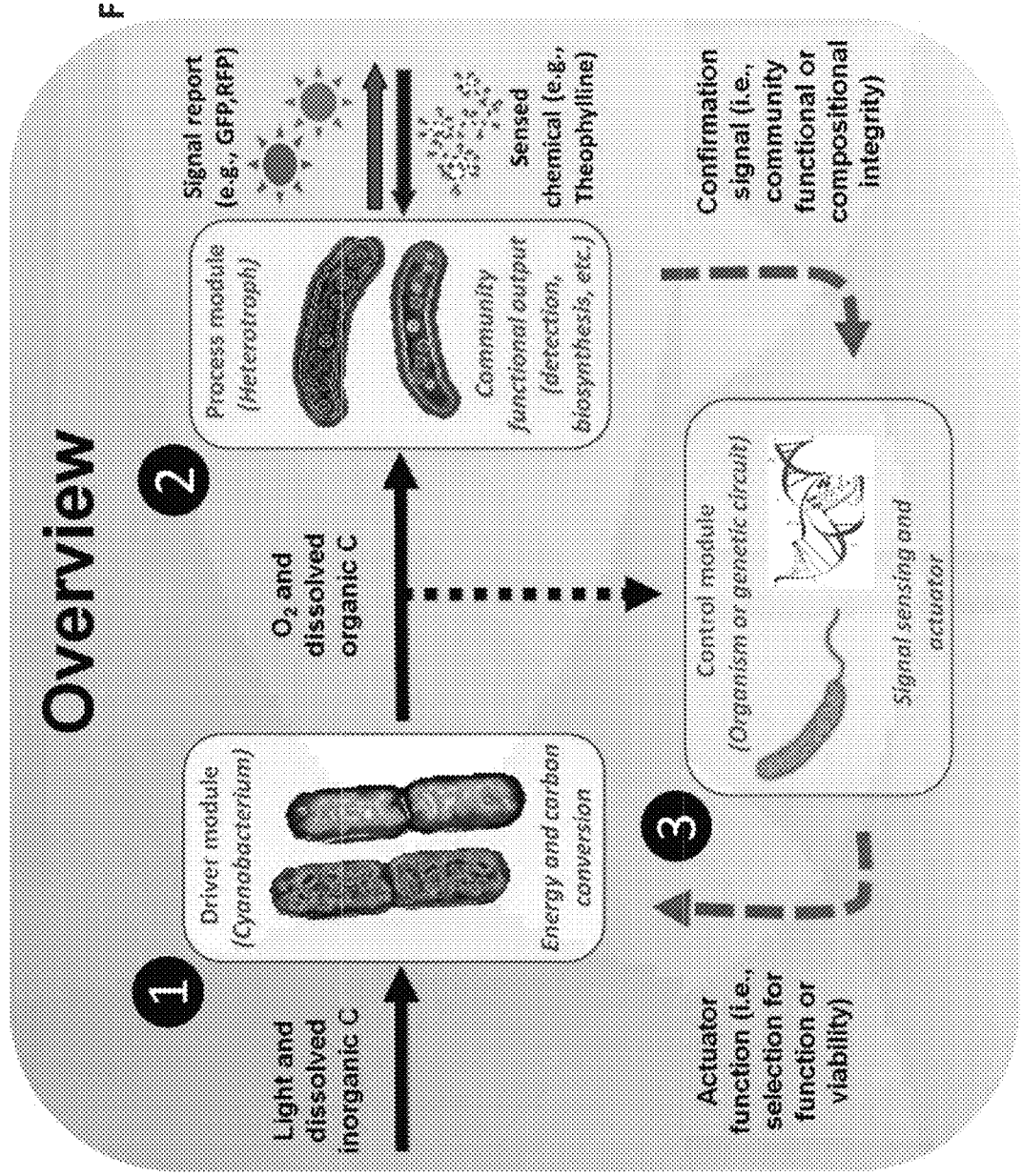
FIGS. 6A-6D provide a schematic of an exemplary self-sustainable, autonomous synthetic microbial consortium that is capable of detecting THP in the environment.

As shown in FIG. 6A, the microbial consortium includes (1) a Driver module comprising a photoautotrophic organism (a cyanobacterium) that provides oxygen and organic carbon to the Process and Control modules; (2) a Process module comprised of a heterotroph that performs the desired function (detection of THP); and (3) a Control module (a heterotroph) that both senses signals from the Process module and actuates activity of the Driver module.

Figure 6B:
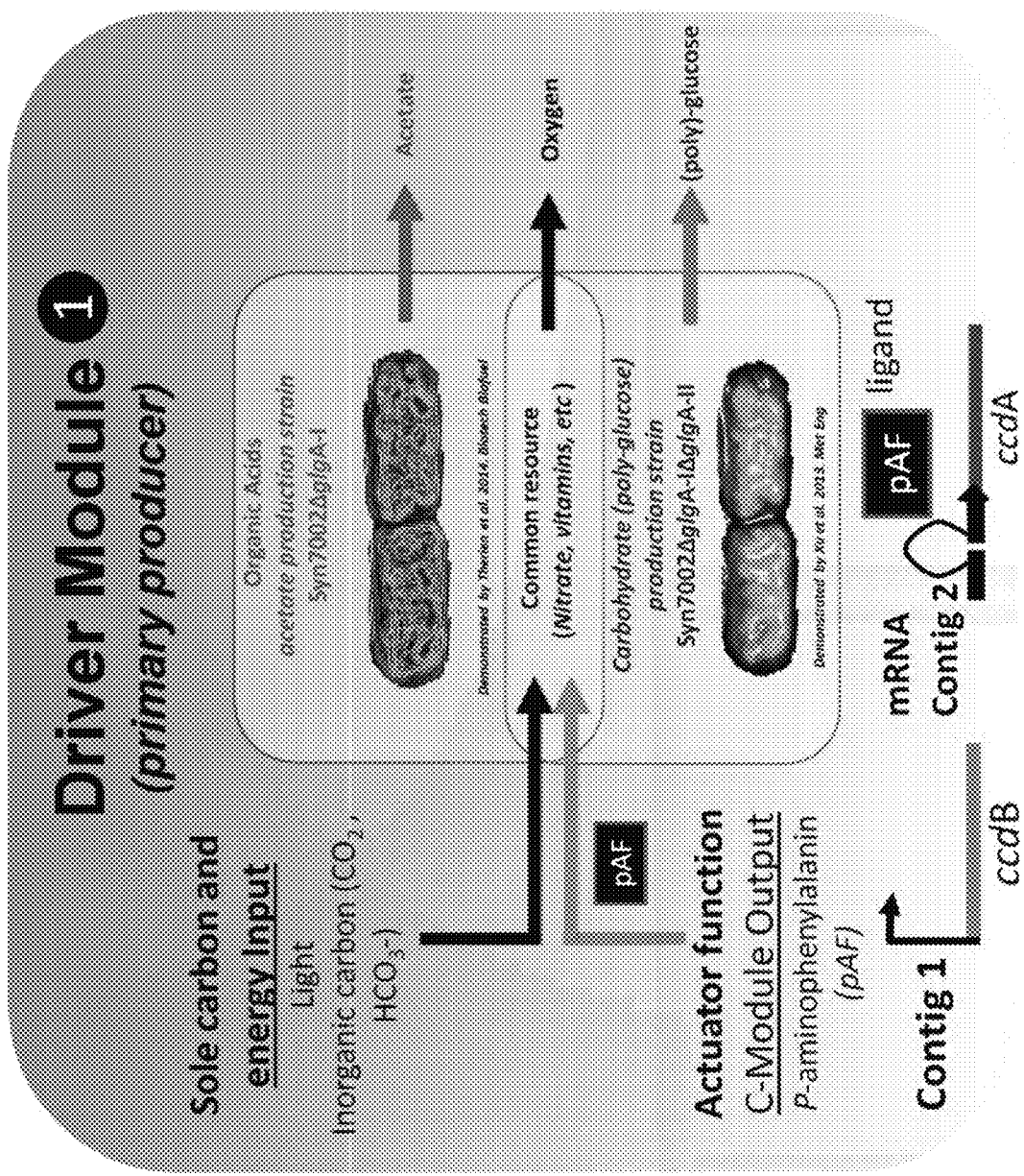

FIG. 6B depicts the Driver module. In this example, the Driver module is comprised of the cyanobacterium *Synechococcus* 7002ΔglgA-I (an acetate production strain) and the cyanobacterium *Synechococcus* 7002ΔglgA-I ΔglgA-II (a carbohydrate production strain). The cyanobacteria utilize light and inorganic carbon (e.g., $CO_2$, $HCO_3^-$) to produce oxygen, acetate and (poly)-glucose that can be used by the other modules. The Driver module also includes nucleic acid constructs encoding a toxin/antitoxin pair. A first construct encodes the CcdB toxin, which is expressed constitutively. A second construct encodes the CcdA antitoxin, the expression of which is regulated by a riboswitch responsive to the ligand pAF. The antitoxin is only expressed when the Control module expresses pAF. Thus, the viability of the Driver module is regulated by the Control module by regulating whether the Driver module expresses the antitoxin to counteract the constitutively expressed toxin.

Figure 6C:
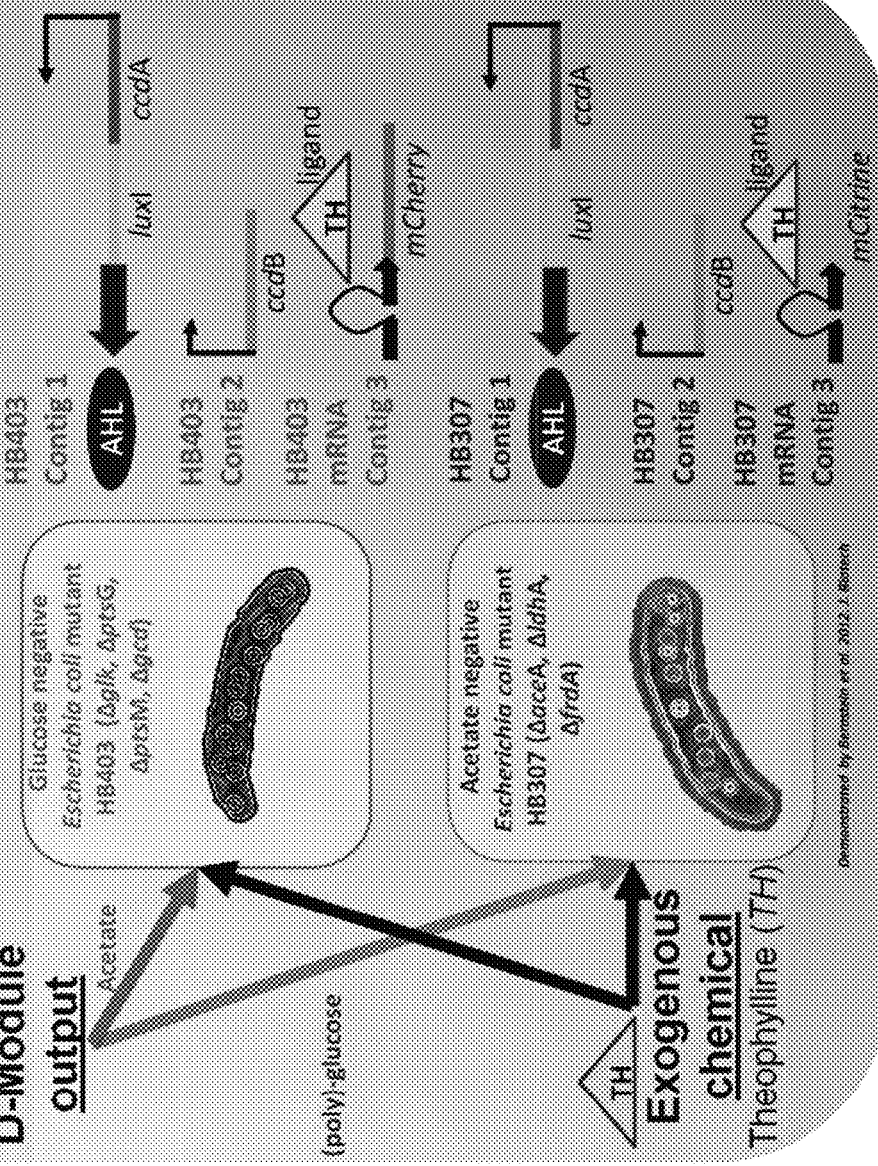

FIG. 6C depicts the Process module. The Process module carries out the desired function of the microbial consortium, which in this case is to detect the presence of exogenous THP. In this example, the Process module is comprised of the glucose-negative *E. coli* mutant HB403 (Δglk, ΔptsG, ΔptsM, Δgcd) and the acetate-negative *E. coli* mutant HB307 (ΔaceA, ΔldhA, ΔfrdA). The glucose-negative and acetate-negative strains utilize the glucose and acetate produced by the Driver module. Each *E. coli* strain produces a unique signaling module, an acyl homoserine lactone (AHL), which is detected by the Control module. Expression of the AHL(s) also triggers expression of the antitoxin CcdA in each *E. coli* strain, while expression of the toxin CcdB is constitutive in each strain. This is carried out through the constitutive production of transcription factors (i.e. LasR or RhlR) that bind to the specific AHL molecules being produced and then, in conjunction with a specific binding sequencing upstream of CcdA (i.e. luxI), drive the expression of the antitoxin gene. In addition, each *E. coli* strain contains a nucleic acid construct expressing a fluorescent protein, the expression of which is regulated by a riboswitch responsive to THP. Therefore, when THP is present in the environment, *E. coli* HB403 expresses mCherry and *E. coli* HB307 expresses mCitrine, providing a detectable readout for the presence of THP.

Figure 6D:
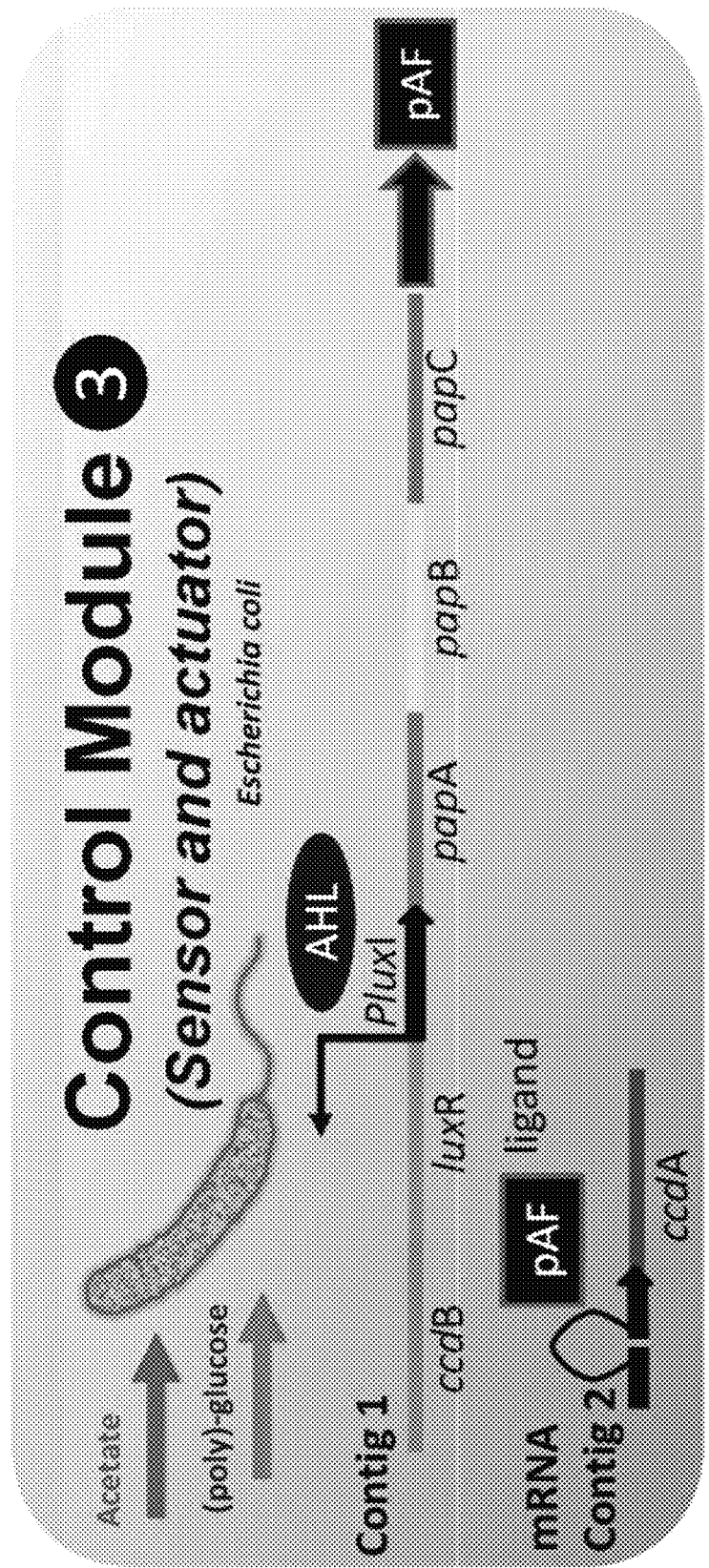

FIG. 6D depicts the Control module. In this example, the Control module is comprised of an *E. coli* strain (a heterotroph) that utilizes the acetate and (poly)-glucose produced by the Driver module. The Control module also contains a nucleic acid construct comprising the pAF operon (papA, papB and papC). pAF is expressed by the pAF operon if the Process module produces one or both of the signaling molecules (the AHLs). Expression of pAF drives expression of the antitoxin CcdA in both the Control module and the Driver module as the expression of CcdA is regulated by a riboswitch responsive to pAF. As with the Driver module, the Control module constitutively expresses the toxin CcdB, therefore, when pAF is not expressed by the Control module, both the Driver module and Control module are not viable.

The riboswitch and pAF operon sequences used in this example are provided below.

```
Theophyllline Riboswitch
                              (SEQ ID NO: 28)
ATTGTGAGCGGATAACAATTACTAGAGATACGACTCACTATAGGTA

CCGGTGATACCAGCATCGTCTTGATGCCCTTGGCAGCACCCTGAGA

AGGGGCAACAAG pAF Riboswitch
                              (SEQ ID NO: 29)
ACGACGACAGGCACCCGAACTCTCTAGAGGGCGAAAGCCGGCGCGT

CCTGGATTCCACCAAGCATGTCCCTACCATACGGGATTGCCCAGCT

TCGGCTGCCATGCCGGCCAAACGGTAACCGGCCTACGGGAGGGGTA

CACAACGCTGATGAGTCCCAAATAGGACGAAACGCGCTAGATCTGA

AAGAGGAGAAATACTAG pAF Operon (papA/B/C)- codon-optimized for
expression in E. coli papA
                              (SEQ ID NO: 30)
atgcgtaccctgctgattgataactatgatagctttacccacaacc tgtttcagtatatcggtgaagcaaccggtcagcctccggttgttgt
```

-continued

```
tccgaatgatgcagattggagccgtctgccgctggaagattttgat
gcaattgttgttagtccgggtccgggtagtccggatcgtgaacgtg
attttggtattagccgtcgtgcaattaccgatagcggtctgccggt
tctgggtgtttgtctgggtcatcagggtattgcacagctgtttggt
ggcaccgttggtctggcaccggaaccgatgcatggtcgtgttagcg
aagttcgtcataccggtgaagatgatttcgtggtctgccgagcccg
tttaccgcagttcgttatcatagcctggcagcaaccgatctgccgg
atgaactggaaccgctggcctggtcagatgatggtgttgttatggg
tctgcgtcatcgtgaaaaaccgctgtgggcaagcagcagcaccggt
gttcatcgtcagcgtctgcgtccgggtgatcatggtcagctgcctc
gtccgcgtccacgtccgcctccgggtacaagtcgtcgtggtcgtct
gcctgttcgtacaccgcgtgcaccgcgtcgtcgtgcagcaggtcgt
cgtcgcggtactccgcgtctgccagcacgtcctcgtgctccgcgta
gcggttggaccgcagcaccgagcagcaaagcaccgcgtgtactgct
gccacgtcgtcgccctcgtccggcacgtcgtgttccgcatctgcct
cgccgtcgtcggcgtcgcctgcgtcctcggctgcgtcgtcatcatg
atccgggtcgtggtgatccgctgcagctgcctggtggtgcagcacg
tacagccggtggtagtcgccgtcctcgtcctgccctgcgtgttcag
ccacgtctgcgtcgtctgccacgcctgcgtgccgaaggtggtgatc
atcgtcgtcctcgtagcaccggtccggctccgcgtcgccgtgttcc
tctgcgtcgcccacgtcatcgtcctcgcccacctggacgtctgctg
ctgcctgcaggaccgcgtcctcctggtccacgtcgccgtcggccac
ggctggcagctggtgatggtcgcgatccgcatcgtcctggccgtcc
acgccctgccgaagcagatccgcgtcatggtctgcgtggtccgcgt
ggtggtggacggctgcgtcctccaggtagccgtaccctcgtcagg
gtcgtctgggtgctccgcagcgtcgtgttgtgcgtgatctgcctga
tcagcatggtcatcgtgcagatcgtggtgacggtccggcagcactg
ctgcgtgcggcacctcatcaaccgcgtccggtttggcgtcctgcac
gcgttccgcgtgcagttggtgcacagcgtctggcacgtgcagttcc
gcatgatcggcgtcgtcgtcgccgtcgtgttcaggcacatcagggt
gatccgccaccgggtcgtaccggtggtggcggtcgtgccgcacctc
gtcgtccaggtcgtcctggtgaaggtcctggtcgtgaaccggatga
tcgccgtccgggacctcagcgtcctcagcagcggctgcgtgatcgt
ctgcgtcctcgtgccctgcactgcgtggtggtcgtccacgtgctc
gtgcaccggcaggcgttgatcatcctggcaccgcagcagcccgtca
tcagcatcgtcggctgcgcacacggcgtctgcctcgtcgtctgcat
gatcgtcgtgcacaagaggcaacccatggtgaccaccgtcctccgg
gtggtcgccctccaggccgtctgacacgtggtgcacgtatggttcg
tccgcaacgcgtcgccgtccgcagcatcgtcatccgcatcatcgt
gccggtcgtcggcctggtcgcgttcggcgtcggcgtggggatcgtg
taccactgcgtcctggcggtggtgtgcaggccgatcgtggtcaggg
tcctcgtcatggccatcgtccacggcgtcagcgtagtggtggccgt
ccgatga
``` papB
(SEQ ID NO: 31)
```
atgaccgaacagaatgaactgcaggttgcagcagcacgtggtgcac
gtcgtccgcgtcgtgatgcaagcggtcatggtgcagcaccgcatcg
tcctcgttgtccgcatcgtgcagttcaggttccggcacgccgtccg
gatgatgcagcacgtcctggtcagccaggtcagggccagggtcgtc
ctctgcgtcgtcgtccacgtcctcgtcgtattgttccgggtgaacc
gctgcgtcgcgatcatcatggtgatgttccgcgtcgcggtccgggt
gatgaacctggtgaaccggatggccgtggtcctggcgaaccggtta
tgtattaa
``` pabC
(SEQ ID NO: 32)
```
atgagcggttttccgcgtagcgttgttgttggtggtagcggtgcag
tgggtggtatgtttgcaggtctgctgcgtgaagcaggtagccgtac
cctggttgttgatctggttccgcctccgggtcgtccggatgcatgt
ctggttggtgatgttaccgcaccgggtccggaactggcagcagcac
tgcgtgatgcagatctggtgctgctggccgttcatgaagatgttgc
actgaaagcagttgcaccggttacccgtctgatgcgtccgggtgca
ctgctggcagatacctgagcgttcgtaccggtatggcagcagagc
tggcagcacatgcaccgggtgttcagcatgttggtctgaatccgat
gtttgcaccggcagcaggtatgacaggccgtccggttgcagcagtt
gttacccgtgatggtcctggtgtgaccgcactgctgcgtctggttg
aaggtggtggtggtcgtcctgttcgtctgacagccgaagaacatga
tcgtaccaccgcagcaacccaggcactgacccatgcagttattctg
agctttggtctggcactggcacgtctgggtgttgatgttcgtgcac
tggcagccaccgcaccgcctccgcatcaagttctgctggccctgct
ggcacgtgttctgggtggtagtccggaagtttatggtgatattcag
cgtagcaatccgcgtgcagcaagcgcacgtcgtgccctggctgaag
ccctgcgtagctttgcagcactgattggtgatgatcctgatcgtgc
cgaagatccggaccgtgcagatgacccggatcgtaccgataatcct
ggtcatccgggtggttgtgatggtgcaggtaatctggatggtgttt
ttgaagaactgcgtcgcctgatgggtcctgagctggctgcaggcca
ggatcattgtcaagaactgtttcgtaccctgcatcgtacagatgat
gaaggtgaaaaagatcgctaa
```

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated microbial consortium, comprising a driver module, a process module and a control module, wherein:
the driver module comprises cyanobacteria comprising:
a first driver module nucleic acid construct that directs constitutive expression of a toxin encoded by ccdB, mazFa, relEs or vapC, and
a second driver module nucleic acid construct encoding a corresponding antitoxin encoded by ccdA, mazEa, relN or vapB, wherein expression of the antitoxin is regulated by a riboswitch responsive to p-amino-phenylalanine (pAF);
the process module comprises Escherichia coli or a species of Shewanella comprising:
a first process module nucleic acid construct encoding a reporter protein or an enzyme, wherein expression of the reporter protein or enzyme is regulated by a riboswitch responsive to theophylline (THP), and
a second process module nucleic acid construct encoding an acly homoserine lactone (AHL); and
the control module comprises a first control module nucleic acid construct encoding pAF, wherein expression of pAF is regulated by the AHL.

2. The microbial consortium of claim 1, wherein the driver cyanobacteria comprises a species of Synechococcus, Cyanothece or Synechocystis.

3. The microbial consortium of claim 1, wherein the driver module toxin and antitoxin are respectively encoded by ccdB and ccdA.

4. The microbial consortium of, claim 1, wherein the process module comprises Escherichia coli.

5. The microbial consortium of claim 1, wherein the reporter protein comprises a fluorescent protein.

6. The microbial consortium of claim 1, wherein the process module further comprises a third process module nucleic acid construct that drives constitutive expression of a toxin encoded by ccdB, mazF, gef, yafO or parE, and a fourth process module nucleic acid construct encoding a corresponding antitoxin encoded by ccdA, mazE, sof, yafN or parD, respectively, wherein expression of the antitoxin is regulated by a riboswitch responsive to AHL.

7. The microbial consortium of claim 6, wherein the process module toxin an antitoxin are respectively encoded by ccdB and ccdA.

8. The microbial consortium of claim 1, wherein the first control module nucleic acid construct is located within the process module.

9. The microbial consortium of claim 1, wherein the control module comprises Escherichia coli or a species of Shewanella comprising the first control module nucleic acid construct.

10. The microbial consortium of claim 9, wherein the control module further comprises a second control module nucleic acid construct that drives constitutive expression of a toxin encoded by ccdB, mazF, gef, vafO or ParE, and a third control module nucleic acid construct ending a corresponding antitoxin encoded by ccdA, mazE, sof yafN or parD, respectively, wherein expression of the antitoxin is regulated by a riboswitch responsive to pAF.

11. The microbial consortium of claim 10, wherein the control module toxin and antitoxin are respectively encoded by ccdB and ccdA.

12. A kit comprising the microbial consortium of claim 1 and growth media, a culture vessel, or both.

13. An isolated microbial consortium, comprising a driver module, a process module and a control module, wherein:
the driver module comprises a species of Synechococcus cyanobacteria comprising:
a first driver module nucleic acid construct that directs constitutive expression of a toxin encoded by ccdB and
a second driver module nucleic acid construct encoding a corresponding antitoxin encoded by ccdA, wherein expression of the antitoxin is regulated by a riboswitch responsive to p-amino-phenylalanine (pAF);
the process module comprises Escherichia coli comprising:
a first process module nucleic acid construct encoding a fluorescent protein, wherein expression of the fluorescent protein is regulated by a riboswitch responsive to theophylline (THP), and
a second process module nucleic acid construct encoding an acyl homoserine lactone (AHL); and
the control module comprises a first control module nucleic acid construct encoding pAF, wherein expression of pAF is regulated by the AHL.

* * * * *

UNITED STATES PATENT AND TRADEMARK OFFICE
CERTIFICATE OF CORRECTION

PATENT NO. : 10,125,348 B2
APPLICATION NO. : 14/991263
DATED : November 13, 2018
INVENTOR(S) : Beliaev et al.

Page 1 of 1

It is certified that error appears in the above-identified patent and that said Letters Patent is hereby corrected as shown below:

In the Claims

Claim 1, Column 37, Line 40, "an acly homoserine" should read –an acyl homoserine–

Claim 7, Column 37, Line 63, "toxin an antitoxin" should read –toxin and antitoxin–

Signed and Sealed this
Twelfth Day of March, 2019

Andrei Iancu
*Director of the United States Patent and Trademark Office*